US010744106B2

(12) United States Patent
Freeman et al.

(10) Patent No.: US 10,744,106 B2
(45) Date of Patent: Aug. 18, 2020

(54) REVERSIBLY PROTECTED THIOLATED ELECTROPHILIC FATTY ACIDS AS PRODRUGS

(71) Applicant: University of Pittsburgh—Of the Commonwealth System of Higher Education, Pittsburgh, PA (US)

(72) Inventors: Bruce A. Freeman, Pittsburgh, PA (US); Nicholas Khoo, Pittsburgh, PA (US); Francisco Jose Schopfer, Pittsburgh, PA (US); Steven Woodcock, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 16/339,702

(22) PCT Filed: Oct. 4, 2017

(86) PCT No.: PCT/US2017/055149
§ 371 (c)(1),
(2) Date: Apr. 4, 2019

(87) PCT Pub. No.: WO2018/067705
PCT Pub. Date: Apr. 12, 2018

(65) Prior Publication Data
US 2019/0282527 A1    Sep. 19, 2019

Related U.S. Application Data

(60) Provisional application No. 62/404,368, filed on Oct. 5, 2016.

(51) Int. Cl.
*A61K 31/20*    (2006.01)
*A61P 3/04*    (2006.01)
(Continued)

(52) U.S. Cl.
CPC ............... *A61K 31/20* (2013.01); *A61P 3/00* (2018.01); *A61P 3/04* (2018.01); *A61P 13/12* (2018.01); *A61P 29/00* (2018.01)

(58) Field of Classification Search
CPC ..................................................... A61K 31/20
(Continued)

(56) References Cited

U.S. PATENT DOCUMENTS 8,324,277 B2    12/2012  Freeman
8,735,449 B2    5/2014   Freeman
(Continued)

FOREIGN PATENT DOCUMENTS

WO    WO 2009/017802    2/2009
WO    WO 2010/014889    2/2010
(Continued)

OTHER PUBLICATIONS

Baker et al., "Nitro-fatty acid reaction with glutathione and cysteine kinetic analysis of thiol alkylation by a Michael addition reaction," *Journal of Biological Chemistry*, 282(42): 31085-31093, Oct. 19, 2007.
(Continued)

*Primary Examiner* — Shengjun Wang
(74) *Attorney, Agent, or Firm* — Klarquist Sparkman, LLP

(57) ABSTRACT

Various embodiments of this invention are directed to pharmaceutical compositions and methods for treating disease. The compositions of such embodiments include thiolated nitro fatty acids. The methods of various embodiments include administering an effective amount of any of these pharmaceutical compositions to a patient in need of treatment.

17 Claims, 7 Drawing Sheets

(51) Int. Cl.
*A61P 13/12* (2006.01)
*A61P 29/00* (2006.01)
*A61P 3/00* (2006.01)

(58) Field of Classification Search
USPC ........................................................ 514/558
See application file for complete search history.

(56) References Cited

U.S. PATENT DOCUMENTS

| | | |
|---|---|---|
| 9,066,902 B2 | 6/2015 | Freeman et al. |
| 9,186,408 B2 | 11/2015 | Freeman et al. |
| 9,700,534 B2 | 7/2017 | Freeman et al. |
| 9,750,725 B2 | 9/2017 | Freeman et al. |
| 10,213,417 B2 | 2/2019 | Freeman et al. |
| 10,258,589 B2 | 4/2019 | Freeman et al. |
| 2015/0018417 A1 | 1/2015 | Freeman et al. |
| 2019/0091186 A1 | 3/2019 | Freeman et al. |

FOREIGN PATENT DOCUMENTS

| | | |
|---|---|---|
| WO | WO 2011/014261 | 2/2011 |
| WO | WO 2013/116753 | 8/2013 |
| WO | WO 2017/151938 | 9/2017 |
| WO | WO 2018/067709 | 4/2018 |

OTHER PUBLICATIONS

International Search Report and Written Opinion issued for International Application No. PCT/US2017/055149 dated Jan. 18, 2018.
Rudolph et al., "Nitro-fatty acid metabolome: saturation, desaturation, beta-oxidation, and protein adduction," *Journal of Biological Chemistry*, 284(3): 1461-1473, Jan. 16, 2009.
Salvatore et al., "Characterization and quantification of endogenous fatty acid nitroalkene metabolites in human urine," *Journal of Lipid Research*, 54(7): 1998-2009, Jul. 1, 2013.
Vitturi et al., "Modulation of nitro-fatty acid signaling prostaglandin reductase-1 is a nitroalkene reductase," *Journal of Biological Chemistry*, 288(35): 25626-25637, Aug. 30, 2013.
U.S. Appl. No. 16/239,425, filed Jan. 3, 2019.
U.S. Appl. No. 16/280,704, filed Feb. 20, 2019.
Supplementary European Search Report issued for EPC Application No. 17859121.0 dated Apr. 23, 2020.
Nishida et al., "Hydrogen sulfide anion regulates redox signaling via electrophile sulfhydration," *Nature Chemical Biology*, vol. 8, pp. 714-724, Jul. 1, 2012.

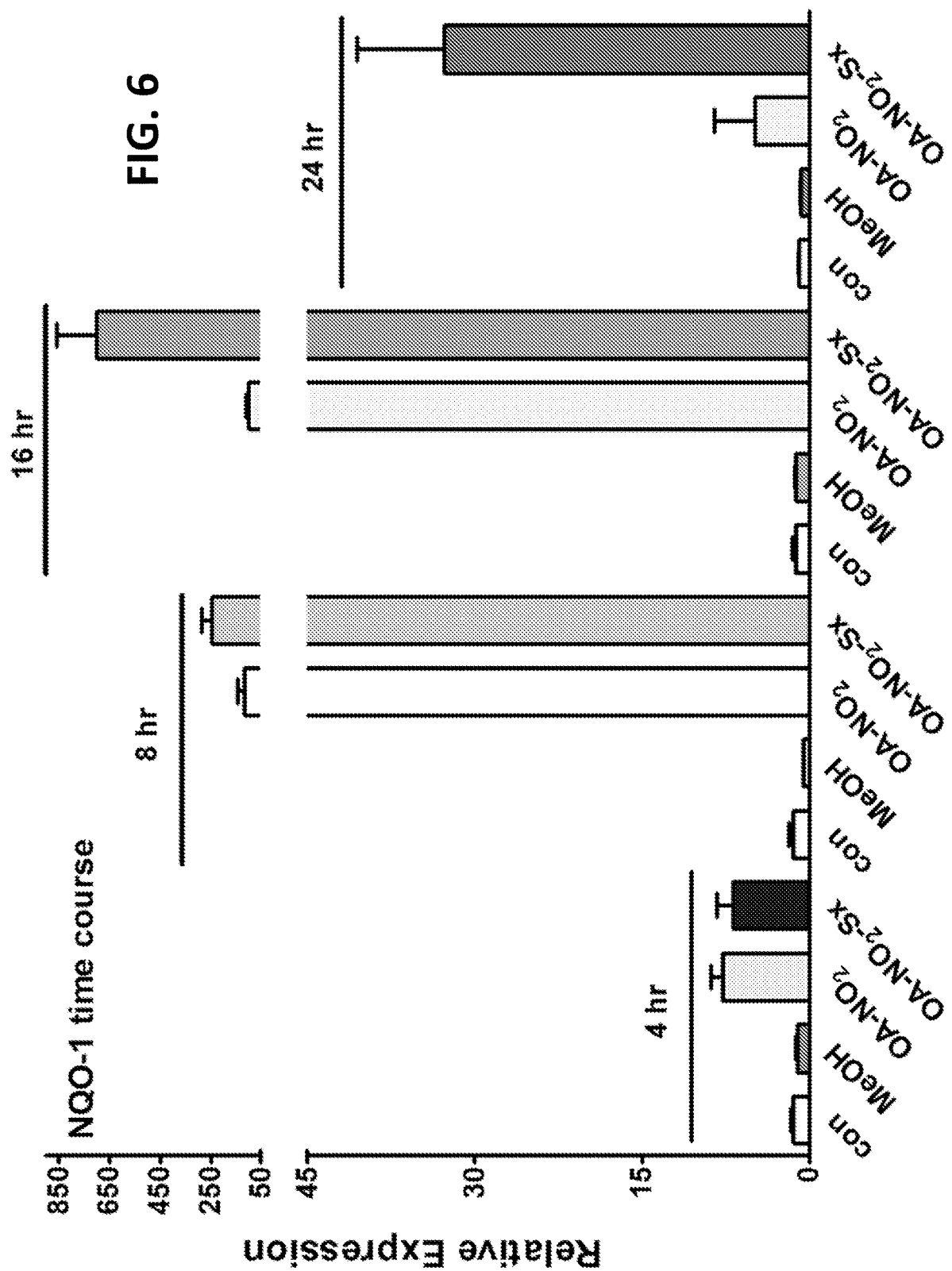

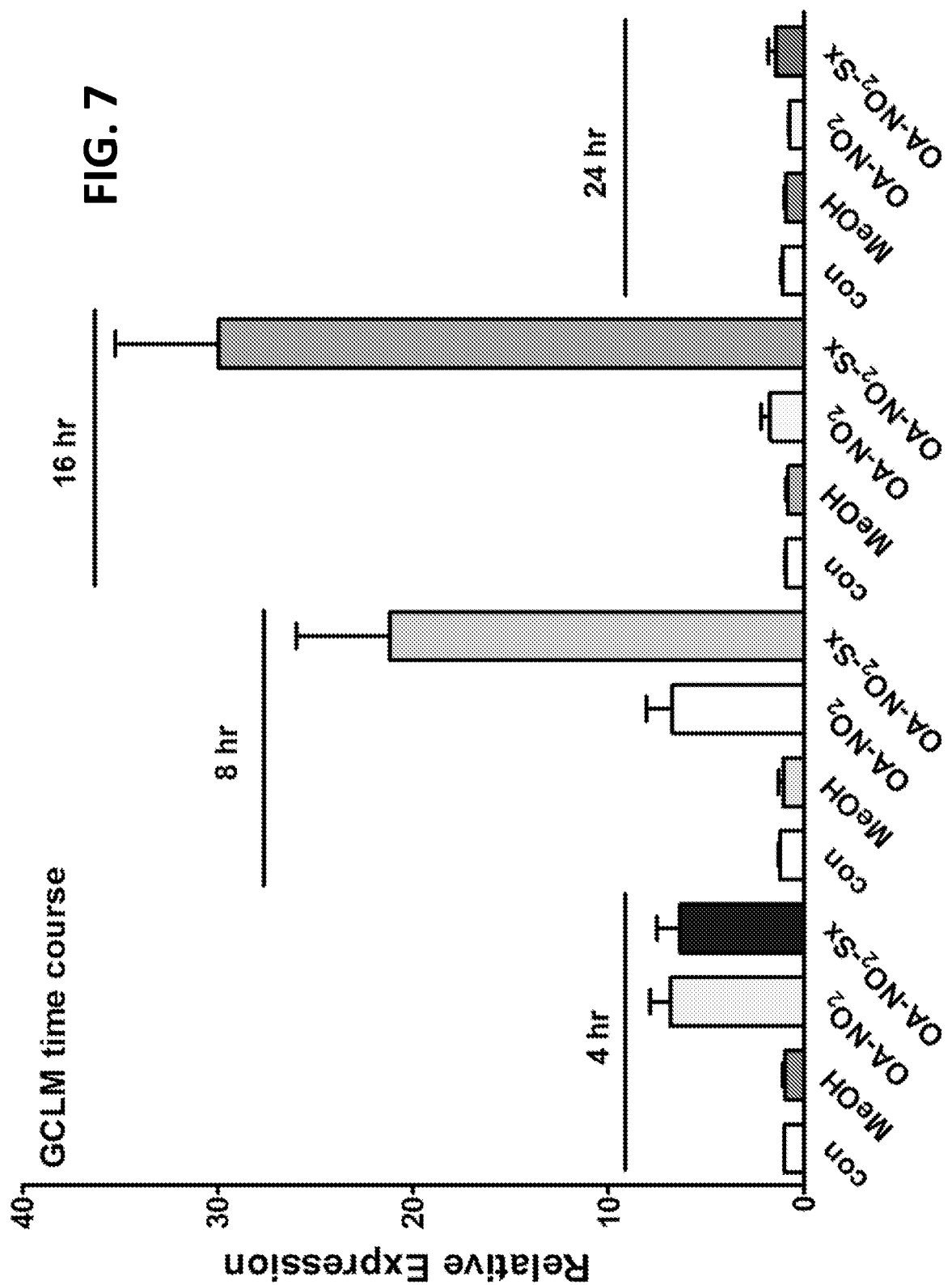

REVERSIBLY PROTECTED THIOLATED ELECTROPHILIC FATTY ACIDS AS PRODRUGS

CROSS REFERENCE TO RELATED APPLICATIONS

This is the U.S. National Stage of International Application No. PCT/US2017/055149, filed Oct. 4, 2017, which was published in English under PCT Article 21(2), which application in turn claims the benefit of U.S. Provisional Application No. 62/404,368, filed Oct. 5, 2016, which is herein incorporated by reference in its entirety.

GOVERNMENT INTERESTS

This invention was made with government support under grant no. HL-058115, HL-064937, and AT006822 awarded by the National Institutes of Health. The United States government has certain rights in the invention.

SUMMARY

Various embodiments of the invention are directed to a synthesis and use of a thiol-adducted nitro fatty acid ("thiolated fatty acid"). Various embodiments of the invention are directed to pharmaceutical compositions comprising an effective amount of a thiolated fatty acid. Various embodiments of the invention are directed to methods for treating inflammation, obesity, metabolic syndrome, acute kidney disease, chronic kidney disease, and reducing gastrointestinal side effects comprising administering to a subject in need thereof an effective amount of thiolated fatty acid.

BRIEF DESCRIPTION OF THE DRAWINGS

FIG. 6: NQO-1 Transcription Induced by $OA-NO_2-S_x$ over time course.
FIG. 7: GCLM Transcription Induced by $OA-NO_2-S_x$ over time course.

DETAILED DESCRIPTION

Figure 1:
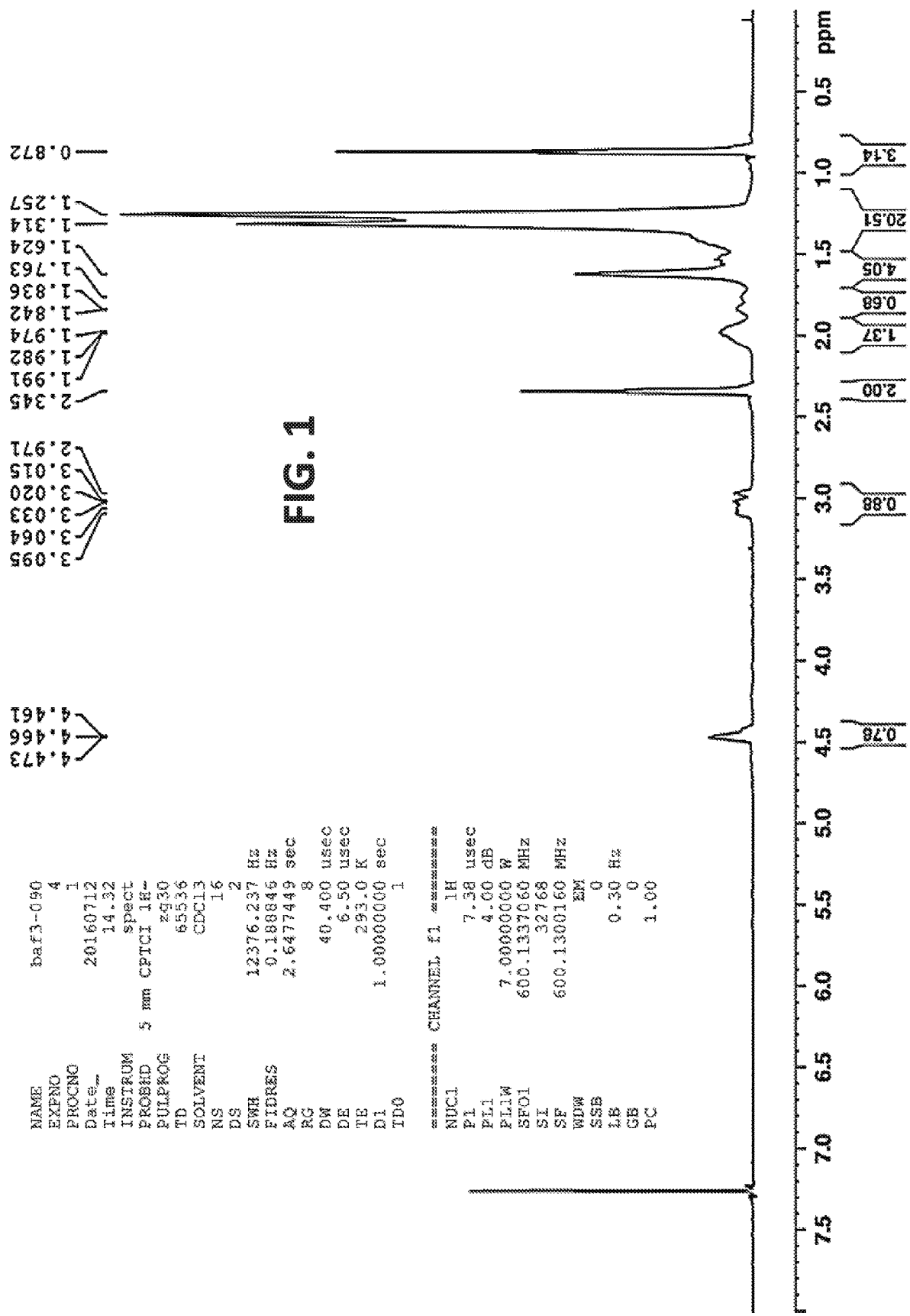
FIG. 1: NMR spectra of $OA-NO_2-S_x$.

This invention is not limited to the particular processes, compositions, or methodologies described, as these may vary. The terminology used in the description is for the purpose of describing the particular versions or embodiments only, and is not intended to limit the scope of the present invention. Unless defined otherwise, all technical and scientific terms used herein have the same meanings as commonly understood by one of ordinary skill in the art. All publications mentioned herein are incorporated by reference in their entirety. Nothing herein is to be construed as an admission that the invention is not entitled to antedate such disclosure by virtue of prior invention.

The term "derivative" refers to a compound that is derived from a similar compound, or a compound that can be imagined to arise from another compound, if one or more atoms are replaced with another atom or group of atoms.

The term "biological sample" refers to tissue, cells, fluids, cellular extract, homogenized tissue extract, or a mixture of one or more enzymes in a suitable physiologically acceptable carrier, such as a mixture that includes without limitation liposomes, albumin and lipoproteins.

The compounds of the invention can exist in various isomeric forms, including configurational, geometric, and conformational isomers, as well as existing in various tautomeric forms, particularly those that differ in the point of attachment of a hydrogen atom and in some constitutional isomers, in which there are variable numbers of repeating units. The term "isomer" is intended to encompass all isomeric forms of a compound of this invention, including tautomeric forms of the compound.

Certain compounds described here may have asymmetric centers and therefore exist in different enantiomeric and diastereomeric forms. The compounds of the invention can be in the form of an optical isomers or a diastereomers. Accordingly, the invention encompasses compounds in the form of their optical isomers, diastereoisomers and mixtures thereof, including a racemic mixture. Optical isomers of the compounds of the invention can be obtained by known techniques such as asymmetric synthesis, chiral chromatography, simulated moving bed technology or via chemical separation of stereoisomers through the employment of optically active resolving agents. Unless otherwise indicated, "stereoisomer" means one stereoisomer of a compound that is substantially free of other stereoisomers of that compound. Thus, a stereomerically pure compound having one chiral center will be substantially free of the opposite enantiomer of the compound. A stereomerically pure compound having two chiral centers will be substantially free of other diastereomers of the compound.

The term "prodrug" denotes a derivative of a compound that can hydrolyze, oxidize, or otherwise react under biological conditions, in vitro or in vivo, to provide an active compound, particularly a compound of the invention. Examples of prodrugs include, but are not limited to, derivatives and metabolites of a compound of the invention that include biohydrolyzable groups such as nitrates, nitrites, nitroso compounds, biohydrolyzable amides, biohydrolyzable esters, biohydrolyzable carbamates, biohydrolyzable thiolates, biohydrolyzable thioesters, biohydrolyzable selenides, and biohydrolyzable phosphate analogues (e.g., monophosphate, diphosphate or triphosphate). For instance, prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by BURGER'S MEDICINAL CHEMISTRY AND DRUG DISCOVERY 6th ed. (Wiley, 2001) and DESIGN AND APPLICATION OF PRODRUGS (Harwood Academic Publishers Gmbh, 1985).

As used herein and in the appended claims, the singular forms "a," "an," and "the" include plural reference unless the context clearly dictates otherwise. Thus, for example, reference to a "cell" is a reference to one or more cells and equivalents thereof known to those skilled in the art, and so forth.

As used herein, the term "about" means plus or minus 10% of the numerical value of the number with which it is being used. Therefore, about 100 mg means in the range of 90 mg-110 mg.

"Administering" when used in conjunction with a therapeutic means to administer a therapeutic to a patient whereby the therapeutic positively impacts the tissue to which it is targeted. Thus, as used herein, the term "administering", when used in conjunction with a compound described herein can include, but is not limited to, providing a compound described herein to a subject systemically by, for example, intravenous injection, whereby the therapeutic reaches the target tissue. "Administering" a composition may be accomplished by, for example, injection, oral administration, topical administration, or by these methods in combination with other known techniques. Administering may be self-administration, wherein the subject in need of such treatment administers a therapeutic or administering may be by a medical or other health care professional or a caretaker of the subject in need of such treatment.

The term "animal," "patient," or "subject" as used herein includes, but is not limited to, humans and non-human vertebrates such as wild, domestic and farm animals.

The term "improves" is used to convey that the present invention changes either the characteristics and/or the physical attributes of the tissue to which it is being provided, applied or administered. The term "improves" may also be used in conjunction with a diseased state such that when a diseased state is "improved" the symptoms or physical characteristics associated with the diseased state are diminished, reduced or eliminated.

The term "inhibiting" includes the administration of a compound of the present invention to prevent the onset of the symptoms, alleviate the symptoms, or eliminate the disease, condition, disorder or a symptom or symptoms thereof.

By "pharmaceutically acceptable", it is meant the carrier, diluent or excipient must be compatible with the other ingredients of the formulation and not deleterious to the recipient thereof.

As used herein, the term "therapeutic" means an agent utilized to discourage, combat, ameliorate, improve, prevent, inhibit, block or reverse an unwanted condition, disease or symptom of a patient as may be indicated by the particular embodiment. In part, embodiments of the present invention are directed to inflammatory conditions, obesity, metabolic syndrome, acute kidney disease, chronic kidney disease, atherogenesis, adipogenesis, neointimal proliferation, kidney injury after ischaemia/reperfusion (I/R) and xenobiotic injury, focal myocardial I/R injury, Ang II-induced systemic hypertension, pulmonary hypertension, cardiac and pulmonary fibrosis, inflammatory bowel disease, nociception, stroke, motor neuron degeneration, diabetes, asthma, COPD, metabolic syndrome, hypertriglyceridemia, fatty liver disease and autoimmune diseases.

A "therapeutically effective amount" or "effective amount" of a composition is a predetermined amount calculated to achieve the desired effect, i.e., to discourage, combat, ameliorate, improve, prevent, inhibit, block, or reverse an unwanted condition, disease or symptom of a patient as may be indicated by the particular embodiment. For example, a "therapeutically effective amount" as recited in a "method of treating" embodiment is a predetermined amount calculated to achieve the desired treatment effect, i.e., to discourage, combat, ameliorate, or improve an unwanted condition, disease or symptom. For example, a "therapeutically effective amount" as recited in a "method of preventing" embodiment is a predetermined amount calculated to achieve the desired treatment effect, i.e., to prevent or inhibit or block an unwanted condition, disease or symptom prior to its occurrence. In part, embodiments of the present invention are directed to inflammatory conditions, obesity, metabolic syndrome, acute kidney disease, chronic kidney disease, atherogenesis, adipogenesis, neointimal proliferation, kidney I/R and xenobiotic injury, focal myocardial I/R injury, Ang II-induced systemic hypertension, pulmonary hypertension, cardiac and pulmonary fibrosis, inflammatory bowel disease, nociception, stroke, motor neuron degeneration, diabetes, asthma, and COPD. The activity contemplated by the present methods includes both medical therapeutic and/or prophylactic treatment, as appropriate. The specific dose of a compound administered according to this invention to obtain therapeutic and/or prophylactic effects will, of course, be determined by the particular circumstances surrounding the case, including, for example, the compound administered, the route of administration, and the condition being treated. However, it will be understood that the effective amount administered will be determined by the physician in the light of the relevant circumstances including the condition to be treated, the choice of compound to be administered, and the chosen route of administration, and therefore, the dosage ranges included herein are not intended to limit the scope of the invention in any way. A therapeutically effective amount of compound of this invention is typically an amount such that when it is administered in a physiologically tolerable excipient composition, it is sufficient to achieve an effective systemic concentration or local concentration in the tissue.

The terms "treat," "treated," "treating," "ameliorate," "improve," or "promote" as used herein refers to both therapeutic treatment and prophylactic or preventative measures, wherein the object is to prevent or slow down (lessen) an undesired physiological condition, disorder or disease, or to obtain beneficial or desired clinical results. For the purposes of this invention, beneficial or desired clinical results include, but are not limited to, alleviation of symptoms of the condition, disorder or disease; diminishment of the extent of the condition, disorder or disease; stabilization (i.e., not worsening) of the state of the condition, disorder or disease; maintain the condition, disorder or disease; delay in onset or slowing of the progression of the condition, disorder or disease; and remission (whether partial or total), whether detectable or undetectable, or enhancement or improvement of the condition, disorder or disease. Amelioration or promotion includes eliciting a clinically significant response without excessive levels of side effects.

Generally speaking, the term "tissue" refers to any aggregation of similarly specialized cells which are united in the performance of a particular function.

Nitro-fatty acids are compounds that are typically elevated in response to oxidative and nitrative stress or in the diet. These compounds have been implicated as potential anti-oxidative and anti-inflammatory therapeutics for a variety of conditions such as inflammatory conditions, obesity, metabolic syndrome, acute kidney disease, chronic kidney disease, atherogenesis, adipogenesis, neointimal proliferation, kidney I/R and xenobiotic injury, focal myocardial I/R injury, Ang II-induced systemic hypertension, pulmonary hypertension, cardiac and pulmonary fibrosis, inflammatory bowel disease, nociception, stroke, motor neuron degeneration, diabetes, asthma, and COPD. Nitro-oleic acid ($NO_2$—OA), in particular, is the subject of many studies. Nitro-oleic acid affects many regulatory pathways, including Nrf2, NF-κB, heat shock factor (HSF), PPAR-γ, which leads to anti-oxidant and anti-inflammatory effects. Also, nitro-oleic acid leads to direct enzyme inhibition of xanthine oxidase, soluble epoxide hydrolase and 5-lipoxygenase. Additional pathways modified by nitro fatty acids include: extracellular signal-regulated kinases, Jun amino-terminal kinases, p38 mitogen-activated protein kinases, signal transducer and activator of transcription 1, TNF receptor associated factor 6 and toll-like receptor 4.

However, one potential barrier to the use of nitro-oleic acid as a drug candidate is its rapid metabolism as a result of beta-oxidation reactions and reduction of the nitroalkene by Prostaglandin Reductase 1, in the liver first pass and reversible adduction with glutathione and excretion. To increase efficacy, the drug must withstand the first pass metabolism. An active drug would be metabolized within the gut microbiome and liver, and thus must be protected in order to appropriately deliver an effective amount of the active drug into circulation.

The modification of $NO_2$—OA by reversible thiolation of the nitroalkene prevents its metabolic inactivation, thus preserving the potential electrophilic character of $NO_2$—OA.

Embodiments of the invention presented herein are generally directed to thiolated electrophilic unsaturated activated fatty acids and, in particular, thiolated unsaturated nitrated fatty acids. As used herein an "activated fatty acid" refers to a fatty acid having at least one electron withdrawing group covalently bound to an unsaturated carbon of the saturated or unsaturated aliphatic chain of a fatty acid. Such activated fatty acids may include an aliphatic chain substituted by any number of electron withdrawing groups at any number of positions on the hydrocarbon chain and such electron withdrawing groups may or may not be associated with a carbon-carbon double bond. Similarly, the thiolated activated fatty acids described herein may include an aliphatic chain having any number of double bonds, which may or may not be associated with an electron withdrawing group, and a sulfur containing group, i.e. a thiol group. In certain embodiments, the sulfur containing group may be positioned at the beta (β) carbon, gamma (χ) carbon, or delta (δ) carbon of the unsaturated aliphatic chain, where the electron withdrawing group is attached to the alpha (α) carbon.

The electrophilic double bond of the nitroalkene is reversibly protected by $H(S)_xR$ forming the thiolated-activated fatty acid. This thiolated-activated fatty acid is now a prodrug and avoids metabolic processes during first pass. The electrophilic double bond is regenerated following the loss of the protective group, as depicted below:

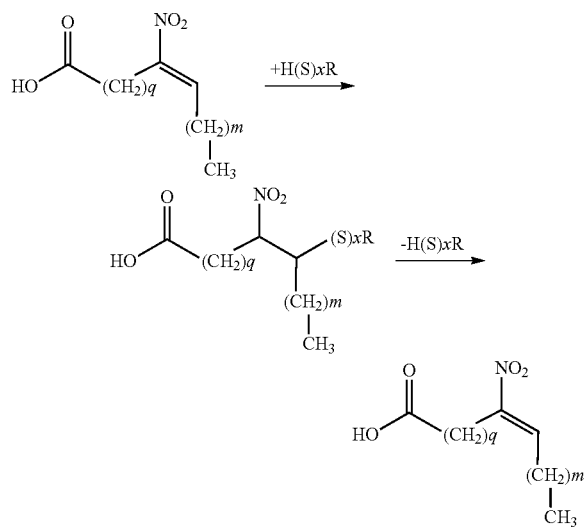

For example, thiolated activated fatty acids of some embodiments may be of general Formula I:

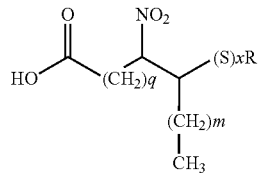

(I)

wherein R is hydrogen (—H), methyl, or $C_2$ to $C_6$ alkyl, alkenyl, or alkynyl, or $(S)xR$ may be a sulfur containing functional group such as, sulfino (—SOOH), sulfo (—SOOOH), or thiocyanate (—SCN), x is an integer from 1 to 5, and q and m are each, independently, an integer from 1 to 10. Compounds of Formula I include a sulfur containing group at the β carbon.

Other thiolated activated fatty acids include compounds of the general Formula II:

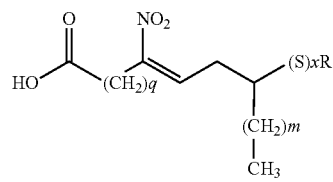

(II)

wherein R is hydrogen (—H), methyl, or $C_2$ to $C_6$ alkyl, alkenyl, or alkynyl, or $(S)xR$ may be a sulfur containing functional group such as, sulfino (—SOOH), sulfo (—SOOOH), or thiocyanate (—SCN), x is an integer from 1 to 5, and q and m are each, independently, an integer from 1 to 10. Compounds of Formula II include a sulfur containing group at the δ carbon.

In some embodiments, R for Formulae I or II may be a bifunctional alkyl, alkenyl, or alkynyl, that is attached to the carboxyl of the activated fatty acid forming bridged or cyclic structures. In such embodiments, the sulfur containing moiety may be positioned at either β, χ, or δ carbon. For example, the compounds of the general Formulae IIIa and IIIb, which include cyclized bifunctional sulfur containing moieties at the β carbon:

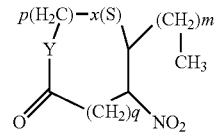

(IIIa)

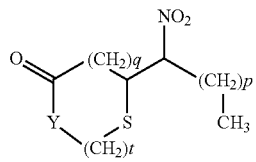

(IIIb)

wherein each Y is, independently, oxygen (O) or nitrogen (N), each x is, independently, an integer from 1 to 5, and q, m, p, and t are each, independently, an integer from 1 to 10.

In some embodiments, the sulfur containing group may join two activated fatty acids. For example, various embodiments of the invention are directed to compounds of the general Formula IV:

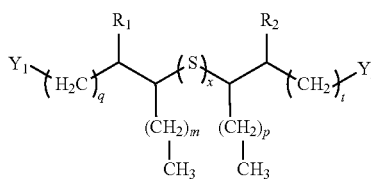

(IV)

wherein $R_1$ and $R_2$ are independently selected from —H and any electron withdrawing groups including, but not limited to —COH, —COR, —COOH, —COOR, —Cl, —F, —Br, —I, —CF$_3$, —CN, —SO$_3$—, —SO$_2$R, —SO$_3$H, —NH$_3^+$, —NH$_2$R$^+$, —NHR$_2^+$, —NR$_3^+$ and —NO$_2$; wherein at least one of $R_1$ and $R_2$ is an electron withdrawing group; wherein $Y_1$ and $Y_2$ are independently selected from H, —COH, —COR, —COOH, and —COOR; wherein at least one of $R_1$ and $R_2$ is an electron withdrawing group; and wherein x is an integer from 1 to 5, and q, m, p, and t are, independently, an integer from 1 to 10, and compositions containing the same.

Various embodiments of the invention are directed to compounds of the general Formulas Va, Vb, and Vc:

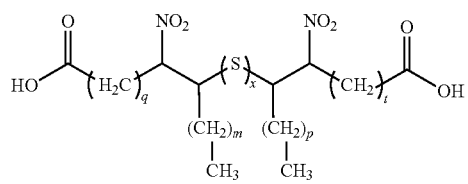

(Va)

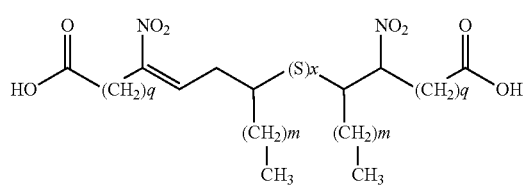

(Vb)

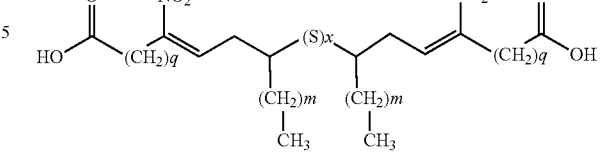

(Vc)

wherein x is an integer from 1 to 5, and q, m, p, and t are, independently, an integer from 1 to 10, and compositions containing the same.

Other embodiments, include compounds of Formula VI:

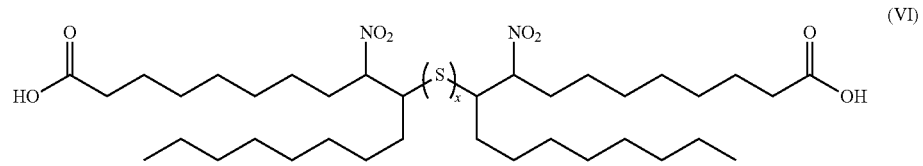

(VI)

wherein x is an integer from 1 to 5, and compositions containing the same.

In some embodiments, the compound is a thiolated nitro-oleic acid (NO$_2$—OA-S$_x$) species depicted as Formula VII:

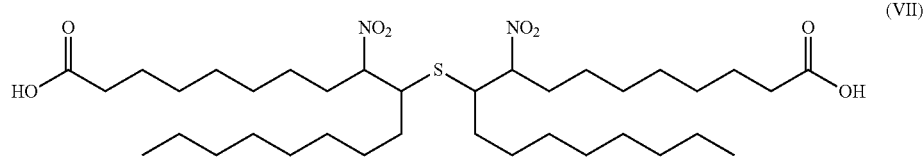 [SMILES: CCCCCCCCC(SC(CCCCCCCC)C(CCCCCCCC(=O)O)[N+](=O)[O-])C(CCCCCCCC(=O)O)[N+](=O)[O-]]

(VII)

The electron withdrawing group may be positioned in either cis or trans configuration in the original double bond or in either R or S absolute stereochemistry at an spa chiral/stereogenic center. For example, in one embodiment, a thiolated activated fatty acid may have one electron withdrawing group, and in another, a thiolated activated fatty acid may be substituted with multiple electron withdrawing groups at multiple positions along the hydrocarbon chain. While the thiolated activated fatty acids of the invention may have an electron withdrawing group positioned at any carbon along the aliphatic hydrocarbon chain between the carboxy terminal carbon to the terminal methyl (ω-position), in some embodiments, the electron withdrawing group may be positioned within about 3 carbons of either the carboxy terminal carbon and/or the methyl terminal carbon, and in other embodiments, the electron withdrawing group may be positioned within 5 carbons of either of the carboxy terminal carbon and/or the methyl terminal carbon. In still other embodiments, the electron withdrawing group may be positioned within 7 carbons of either of the carboxy terminal carbon and/or the methyl terminal carbon, and in further embodiments, the electron withdrawing group may be positioned within 9 carbons of either of the carboxy terminal carbon and/or the methyl terminal carbon.

In certain embodiments, the electron withdrawing group may be positioned on a carbon originating from a double bond of the activated fatty acid forming an "electron withdrawing vinyl" group. The electron withdrawing group of such vinyl groups may be on either side of the double bond. Fatty acids encompassed by embodiments of the invention may have one or more than one electron withdrawing vinyl groups at any carbon on the aliphatic hydrocarbon chain, and there are several ways that an unsaturated fatty acid can have one electron-withdrawing group. In one embodiment, a thiolated activated oleic acid (octadec-9-enoic acid) which originates from an 18 carbon, ω-9 fatty acid with one double bond (denoted "18:1") between the 9h (C-9) and 10th (C-10) carbons, may have an electron withdrawing group at either C-9 or C-10, and a thiol (—SR) at the alternate position. In another exemplary embodiment, a thiolated activated linoleic acid (octadeca-9,12,-dienoic acid), which originated from an 18 carbon, ω-6 fatty acid with two double bonds (denoted "18:2") between the ω-6 (C-13) and -7 (C-12) carbons and the ω-9 (C-10) and 10 (C-9) carbons, may have an electron withdrawing group at C-9 or C-10, or C-12 or C-13, and a thiol (—SR) at the corresponding alternate neighboring position. Similarly, other polyunsaturated fatty acids, originally having 3, 4, 5, 6 or more double bonds, can have one electron withdrawing at either position on any of the original double bond carbons, and a thiol (—SR) at the corresponding alternate neighboring position, including all possible permutations of positions and electron withdrawing groups.

In other embodiments, a mono or polyunsaturated fatty acid may have two electron-withdrawing groups, and there are several ways that an unsaturated fatty acid can have two electron-withdrawing groups. For example, in one embodiment, a thiolated activated linoleic acid (octadeca-9,12,-dienoic acid), which originates from an 18 carbon, ω-6 fatty acid with two double bonds (denoted "18:2") between the ω-6 (C-13) and -7 (C-12) carbons and the ω-9 (C-10) and 10 (C-9) carbons, may have an electron withdrawing group at any two of the positions C-9, C-10, C-12 or C-13, with the following possible permutations: C-9 and C-12, C-9 and C-13, C-10 and C-12, or C-10 and C-13, and one or more thiols (—SR) at the corresponding alternate neighboring positions.

In analogy to the preceding descriptions of compounds with one electron withdrawing group or two electron-withdrawing groups, it is also possible to have three, four, five or more electron withdrawing groups. Following the same logic above, in the preceding descriptions of compounds with one electron-withdrawing group or two electron-withdrawing groups, polyunsaturated fatty acids, with 3, 4, 5, 6 or more double bonds, conjugated or non-conjugated, can have multiple electron withdrawing (three, four, five or more, as available positions for substitution permit) at any of the positions on any of the double bond carbons, including all possible permutations of positions, nucleophilic substituents, and electron-withdrawing groups. Additionally, in any embodiments such as those described above, any number of non-electron-withdrawing groups may be covalently bound to carbons of the aliphatic chain of the activated fatty acid. For example, in some embodiments, the thiolated activated fatty acids of the invention may include one or more methyl, $C_2$-$C_6$ alkyl, alkenyl, or alkynyl or amino covalently attached to one or more carbons of the aliphatic chain of a thiolated activated fatty acid.

The term "electron-withdrawing group" is recognized in the art and denotes the tendency of a substituent to attract valence electrons from neighboring atoms, i.e., the substituent is electronegative with respect to neighboring atoms. The term "nucleophile" or "electron-donating group" is recognized in the art and denotes the tendency of a substituent to donate excess valence electrons from neighboring atoms, i.e., the substituent is electropositive with respect to neighboring atoms. A quantification of the level of electron withdrawing capability is given by the Hammett sigma (σ) constant (see, e.g., J. March, Advanced Organic Chemistry, McGraw Hill Book Company, New York, (1977 edition) pp. 251-259). The Hammett constant values are generally negative for electron donating groups and positive for electron withdrawing groups. For example the Hammet constant for para substituted $NH_2$ (σ [P]) is about −0.7 and the σ [P] for a nitro group is about +0.8.

Embodiments of the invention encompass any known electron withdrawing group. For example, electron-withdrawing groups may include, but are not limited to, aldehyde (—COH), acyl (—COR), carboxylic acid (—COOH), ester (—COOR), halides (—Cl, F, —Br, etc.), fluoromethyl (—$CF_3$), fluoroalkyl (—$CF_nH_{2-n}R$), cyano (—CN), sulfoxide (—SOR), sulfonyl (—$SO_2R$), sulfonate ($SO_3R$), 1°, 2° and 3° ammonium (—$NR_3^+$), and nitro (—$NO_2$) where each R may, independently, be hydrogen, methyl, or $C_2$ to $C_6$ alkyl, alkenyl, or alkynyl. In some embodiments, the electron withdrawing group may be a strong electron withdrawing group having a σ of at least about 0.2, and in certain embodiments, the electron withdrawing group may form a dipole. For example, in particular embodiments, the electron withdrawing group may be a nitro, ammonium or sulfonyl. In other embodiments, the thiolated activated fatty acids of the invention may be additionally substituted by non-electron withdrawing groups or electron donating groups including, for example, thiol (—SR), alcohol (—OH), reverse ester (—OOCR), alkyl, alkenyl, alkynyl, 1° and 2° amines (—$NR_2$), N-containing heterocycle (—N=, —NR—), nitrate (—$ONO_2$), nitrito (—ONO) and the like.

The fatty acids of embodiments may be any unsaturated and polyunsaturated fatty acid known in the art. The term "fatty acid" describes aliphatic monocarboxylic acids. Various embodiments include activated fatty acids having an aliphatic hydrocarbon chain identical or similar to identified, naturally occurring fatty acids. For example, aliphatic hydrocarbon chains of known naturally occurring fatty acids are generally unbranched and contain an even number of from about 4 to about 24 carbons, and others include fatty acids having from 12 to 18 carbons in the aliphatic hydrocarbon chain. In still other embodiments, fatty acids may have greater than 24 carbons in the aliphatic hydrocarbon chain. Embodiments of the invention encompass such naturally occurring fatty acids as well as non-naturally occurring fatty acids, which may contain an odd number of carbons and/or a non-naturally occurring linker including heteroatoms. Thus, some embodiments of the invention include fatty acids having an odd number of carbons of, for example, from 5 to 23 carbons, and in other embodiments, from 11 to 17 carbons. In yet other embodiments, the fatty acids of embodiments may have greater than 23 carbons. The naturally and non-naturally occurring fatty acids of the invention may also be branched at one or more location along the hydrocarbon chain, and in various embodiments, each branch may include an aliphatic hydrocarbon chain of from 1 to 24 carbons, 2 to 20 carbons or 4 to 18 carbons wherein each branch may have an even or odd number of carbons.

The aliphatic hydrocarbon chain of fatty acids of various embodiments may be unsaturated or polyunsaturated. The term "unsaturated" refers to a fatty acid having a aliphatic hydrocarbon chain that includes at least one double bond and/or substituent. In contrast, a "saturated" hydrocarbon chain does not include any double bonds or substituents. Thus, each carbon of the hydrocarbon chain is 'saturated' and has the maximum number of hydrogens. "Polyunsaturated," generally, refers to fatty acids having hydrocarbon chains with more than one double bond. The double bonds of the unsaturated or polyunsaturated fatty acids of various embodiments may be at any location along the aliphatic hydrocarbon chain and may be in either cis or trans configuration. The term "cis," refers to a double bond in which carbons adjacent to the double bond are on the same side and the term "trans" refers to a double bond in which carbons adjacent to the double bond are on opposite sides. Typically "cis" is the same as Z, and "trans" is the same as E but sometimes the IUPAC rules for naming compounds will give the opposite of this for non-carbon substituents, which is the typical case in nitroalkenes. For example, a nitroalkene can have the two carbon groups "cis" but the two groups that take priority for the naming of compounds (a nitro group on one carbon of the alkene and a carbon group on the other carbon of the alkene) are on opposite sides and thus are E. Therefore the nitroalkene analog of a "cis" double bond is termed an E nitroalkene. Similarly, the nitroalkene analog of a "trans" double bond is termed a Z nitroalkene. Without wishing to be bound by theory, double bonds in cis configuration along the carbon chain (cis carbon chain but E nitroalkene) may induce a bend in the hydrocarbon chain. Double bonds in "trans," configuration along the carbon chain (trans carbon chain but Z nitroalkene) may not cause the hydrocarbon chain to bend. Embodiments of the invention may include thiolate activated fatty acids having double bonds in either cis or trans configuration, and encompass compositions that may include combinations of cis and trans containing thiolated activated fatty acids and regioisomers of the thiolated activated fatty acids.

Many unsaturated and polyunsaturated fatty acids have been identified and are known to be naturally occurring. Such unsaturated or polyunsaturated naturally occurring fatty acids, generally, include an even number of carbons in their aliphatic hydrocarbon chain. For example, a naturally occurring unsaturated or polyunsaturated fatty acid may have, 4, 6, 8, 10, 12, 14, 16, 18, 20, 22 and so on carbons and may include omega ($\omega$)-3, $\omega$-5, $\omega$-6, $\omega$-7, $\omega$-9 carbon-carbon double bonds. Any such fatty acid may be useful in embodiments of the invention. The symbol '$\omega$' is used to refer to the terminal methyl carbon of the aliphatic hydrocarbon chain. The placement of the double bond of the $\omega$-X fatty acid is the carbon-carbon bond X number of carbons from the $\omega$ carbon. For example, an $\omega$-6 fatty acid has a double bond between the $6^{th}$ and 7th carbons counting backward from the $\omega$-carbon and an $\omega$-3 fatty acid has a double bond between the 3rd and 4th carbons counting backward from the $\omega$-carbon. Various embodiments of the invention include nitrated $\omega$-3 fatty acids, including, but not limited to, linolenic acid, alphalinolenic acid, eicosapentanoic acid, docosapentaenoic acid, docosahexaenoic acid and stearidonic acid; nitrated $\omega$-5 fatty acids including, but not limited to, myristoleic acid; nitrated $\omega$-6 fatty acids including, but not limited to, linoleic acid, gamma-linoleic acid, dihomo-gamma-linoleic acid and arachidonic acid; nitrated $\omega$-7 fatty acids including, but not limited to, conjugated linoleic and palmitoleic acid; and nitrated $\omega$-9 fatty acids including, but not limited to, oleic acid and erucic acid. Of course, the fatty acids of the invention may also be referred to using IUPAC nomenclature in which the placement of the double bond is determined by counting from the carbon of the carboxylic acid, and 'C—X' denotes the carbon in aliphatic hydrocarbons using IUPAC nomenclature wherein X is the number of the carbon counting from the carboxylic acid (including the carbonyl carbon itself). Embodiments of the invention also include synthetic equivalents to naturally occurring fatty acids and derivatives thereof.

Other embodiments of the invention include unsaturated or polyunsaturated nonnaturally occurring fatty acids which may have an odd number of carbons such as, for example, 5, 7, 9, 11, 13, 15, 17, 19, 20, 21 and so on. As in naturally occurring fatty acids, the one or more double bonds associated with non-naturally occurring fatty acids may be at any position along the aliphatic hydrocarbon chain, and the double bonds may be in either cis or trans configuration. In yet other embodiments, the non-naturally occurring fatty acids may include one or more linker groups, which interrupt the aliphatic hydrocarbon chain. For example, in some embodiments, activated fatty acids may have one or more non-carbon-carbon linkage such as, for example, ester, ether, vinyl ether, thioether, amino, imine and the like at any position within the aliphatic hydrocarbon chain.

Various embodiments of the invention include unsaturated or polyunsaturated fatty acids that may have a carbon-carbon double bond between any two carbons of the aliphatic chain of the fatty acid, and any number of carbon-carbon double bonds may be present in such polyunsaturated fatty acids. For example in some embodiments, polyunsaturated fatty acids may have 2, 3, 4, 5, 6 or more carbon-carbon double bonds. In such embodiments, each of the more than one carbon-carbon double bond may individually be in either cis or trans configuration. In some embodiments, thiolated activated fatty acids are derived from reaction with at least one of the carbon-carbon double bonds of a polyunsaturated fatty acid which has an associated electron withdrawing group, and in other embodiments, more than one of the carbon-carbon double bonds of such polyunsaturated fatty acids may have an associated electron withdrawing group. Additionally, in such embodiments, the electron withdrawing group may be associated with either carbon of the original carbon-carbon double bond or a carbon directly adjacent to either carbon of the carbon-carbon double bond, and the thiol may be associated with the other carbon of the original carbon-carbon double bond or a carbon directly adjacent to either carbon of the carbon-carbon double bond. For example, in some embodiments, an electron withdrawing group may be attached to the alpha ($\alpha$) carbon of the former carbon-carbon double bond, and in other embodiments, an electron withdrawing group may be associated with the beta ($\beta$) carbon of the former carbon-carbon double bond. In those embodiments, a thiol would be attached respectively to the beta ($\beta$) carbon of the former carbon-carbon double bond, and in other embodiments, an electron withdrawing group may be associated with the alpha ($\alpha$) carbon of the former carbon-carbon double bond.

In particular embodiments, an unsaturated fatty acid having at least one electron withdrawing group may be a conjugated fatty acid. In such embodiments, two carbon-carbon double bonds in an aliphatic chain are adjacent to one another such that there is no methylene group between them. Such conjugated compounds are commonly called 1,3-dienes, or conjugated fatty acids. Such 1,3-dienes may include one or more electron withdrawing groups at any of 6 positions, at the 1, 2, 3, and/or 4 positions of the 1,3-dienes and at the two carbons adjacent to the diene (at the 0 and 5 positions, in relation to the 1, 2, 3, 4 method of identifying carbons in a 1,3-diene). For example, one associated electron withdrawing group may be attached to any of the 6 positions identified above, that is to either the 1, 2, 3, or 4 positions on the diene or to either of the carbons adjacent to the 1,3-diene (at the 0 or 5 positions, as described above). In additional embodiments, two associated electron withdrawing groups could be attached to any two of the six possible positions, three associated electron withdrawing groups could be attached to any two of the six possible positions, four associated electron withdrawing groups could be attached to any two of the six possible positions, five associated electron withdrawing groups could be attached to any two of the six possible positions, and six associated electron withdrawing groups could be attached to any two of the six possible positions. In summary, any configuration of electron withdrawing groups attached to any of the six positions described above in a 1,3-diene are encompassed by embodiments of the invention.

In certain embodiments, the thiolated activated fatty acids of the invention may undergo an isomerization following preparation such that either the cis/trans configuration of the double bond, the location of the double bond in the carbon chain, or both, may change. For example, in some embodiments, a thiolated activated fatty acid may be prepared from a carbon-carbon double bond of having an electron withdrawing group attached to a gamma carbon of a carbon-carbon double bond. Following preparation, the carbon-carbon double bond may undergo an isomerization such that the electron withdrawing group is now conjugated with the carbon-carbon double bond after isomerization. Such isomerizations may occur spontaneously at any time following preparation, and may result in a composition which may have initially been prepared as including a single species of a thiolated activated fatty acid that subsequently includes a combination of isomers of the first-prepared activated fatty acid originally produced.

In still other embodiments, the carboxy-terminal end of the thiolated activated fatty acid may be modified. For example, in some embodiments, the thiolated activated fatty acid may include a glycerol associated with the carboxy-terminal end of the fatty acid to create a glycerolipid, and such glycerolipids may be mono-, di-, or tri-glycerides wherein at least one of the fatty acids of a di or tri-glyceride may be a thiolated activated fatty acid and any remaining fatty acids may be a saturated or unsaturated fatty acid. Similarly, in other embodiments, a carbohydrate may be associated with the carboxy-terminal end of a thiolated activated fatty acid to form a glycolipid. In such embodiments, any carbohydrate known in the art may be a carbohydrate moiety of a glycolipid including, but not limited to, galactose and glucose. In yet other embodiments, a carbohydrate may be associated with a glyceride which is associated with the carboxy-terminal end of a thiolated activated fatty acid to form a glycero-glycolipid, which may have one or two activated fatty acids associated with the glycero-portion of the glycero-glycolipid and, in embodiments in which only one activated fatty acid is associated with the glycero-glycolipid, the remaining position on the glycerol may include a saturated or unsaturated fatty acid or hydrogen, alkyl, or a functional group such as, for example, alcohol, amine, phosphate, phosphonic acid, thiol, sulfonic acid and the like. In certain embodiments, the carboxy-terminal end of the activated fatty acids of the invention may be associated with a phosphate to form a phospholipid. In such embodiments, the phosphate may be directly associated with the fatty acid through the carboxy-terminus, or the phosphate may be associated with a di-glyceride wherein one or two activated fatty acids are attached glycerol moiety and, in embodiments where only one thiolated activated the fatty acid is attached to the glycerol, remaining position on the glycerol may include a saturated or unsaturated fatty acid or hydrogen, alkyl, or a functional group such as, for example, alcohol, amine, phosphate, phosphonic acid, thiol, sulfonic acid and the like. In further embodiments, the carboxy-terminus of the activated fatty acid may be associated with a cholesterol or other sterol moiety. In yet other embodiments, the carboxy-terminal end may be modified by the covalent attachment of a secondary active agent. In the particular embodiments, carboxy-terminal modifications including a glycerol may not include a nitro group. Without wishing to be bound by theory, modification of the carboxy-terminal end of thiolated activated fatty acids may enhance partitioning of the activated fatty acid after administration and may also improve resilience of the activated fatty acid by inhibiting beta-oxidation in mitochondria following administration.

The compounds of the present invention increase the bioavailability of the activated fatty acid present as a dimer within the thiolated molecule. Thiolation of the electrophilic alkene protects the molecule through the first pass metabolism of the intestinal tract and liver. This protection occurs by preventing reduction of the alkene by Prostaglandin Reductase 1 and by delaying the adduction with glutathione. Further, the longer polysulfide chain the greater the stability of the molecule, providing for an extended release of the activated fatty acid in circulation. When the thioloated nitro fatty acid releases the nitro fatty acid and a hydrogen sulfide, an additional protective measure is provided.

In some of the embodiment presented herein, the thiolated fatty acid releases hydrogen polysulfide and in at least one embodiment releases hydrogen sulfide. Hydrogen sulfide ($H_2S$), along with nitric oxide and carbon monoxide, is a biologically active gas commonly referred to as a gasotransmitter or gasomediator. $H_2S$ is synthesized from cysteine inside the cell by cystathionine $\gamma$ lyase, cystathionine $\beta$ synthetase, or 3-mercaptopyruvate sulfurtransferase as an extension of the transsulfuration pathway and is mainly found in its anionic form $HS^-$. The reactivity of $HS^-$ is primarily influenced by its reducing and nucleophilic properties, as well as the ability of sulfur to form complexes with transition metals. $H_2S$ modifies proteins, modulates ion channel function, inhibits apoptosis and limits oxidative stress in endothelial cells, smooth muscle cells, inflammatory cells, mitochondria, endoplasmic reticulum and nuclear transcription factors. Specifically, $H_2S$ activates KATP and transient receptor potential (TRP) channels and inhibits big conductance $Ca^{2+-}$ sensitive $K^+$ (BKCa) channels, T-type calcium channels, and M-type calcium channels as well as alters NF-κB nuclear translocation and numerous kinases including p38, ERK and Akt. These altered cellular and metabolic pathways have been implicated in improved cardiovascular homeostasis and health. H2S actively participates in the protection of blood vessels, blood pressure regulation and protects against myocardial injury and inflammation.

In some embodiments, the thiolated fatty acid can be administered to achieve physiological and/or pharmacological levels of $H_2S$ to protect blood vessels, regulate blood pressure and limit both myocardial injury and inflammation. The thiolated fatty acid will release $H_2S$ in the circulation to protect distal organs from inflammation, ischemia and reperfusion, hipoperfusion, anoxia and hypoxia and maintain vascular homeostasis.

In embodiments described herein, the therapeutically effective amount of a thiolated activated fatty acid is from about 5 milligrams to about 5000 milligrams. In the various embodiments described above, a therapeutically effective amount of a thiolated activated fatty acid may be as a daily dose or a single dose within a range of a lower limit amount and an upper limit amount. In some embodiments, the lower limit amount is about 5 mg, about 10 mg, about 25 mg, about 50 mg, about 75 mg, about 100 mg, about 125 mg, about 150 mg, about 175 mg, about 200 mg, about 225 mg, about 250 mg, about 275 mg, about 300 mg, about 325 mg, about 350 mg, about, 375 mg, about 400 mg, about 425 mg, about 450 mg, about 475 mg, about 500 mg, about 525 mg, about 550 mg, about 575 mg, about 600 mg, about 625 mg, about 650 mg, about 675 mg, about 700 mg, about 725 mg, about 750 mg, about 775 mg, about 800 mg, about 825 mg, about 850 mg, about 875 mg, about 900 mg, about 925 mg, about 950 mg, about 975 mg, about 1000 mg, about 1500 mg, about 2000 mg, about 2500 mg, about 3000 mg, about 3500 mg, about 4000 mg, about 4500 mg. In some embodiments, the upper limit amount is about 5000 mg, about 4500 mg, about 4000 mg, about 3500 mg, about 3000 mg, about 2500 mg, about 2000 mg, about 1500 mg, 1000 mg, about 975 mg, about 950 mg, about 925 mg, about 900 mg, about 875 mg, about 850 mg, about 825 mg, about 800 mg, about 775 mg, about 750 mg, about 725 mg, about 700 mg, about 675 mg, about 650 mg, about 625 mg, about 600 mg, about 575 mg, about 550 mg, about 525 mg, about 500 mg, about 475 mg, about 450 mg, about 425 mg, about 400 mg, about 375 mg, about 350 mg, about 325 mg, about 300 mg, about 275 mg, about 250 mg, about 225 mg, about 200 mg, about 175 mg, about 150 mg, about 125 mg, about 100 mg, about 75 mg, or about 50 mg. In some embodiments, the daily dose may be any range between an upper and a lower limit of ranges previously disclosed. In some embodiments, the daily dose may be from about 25 mg to less than about 450 mg, about 25 mg to about 425 mg, about 25 mg to about 400 mg, about 25 mg to about 375 mg, about 25 mg to about 350 mg, about 25 mg to about 325 mg, about 25 mg to about 300 mg, about 25 mg to about 275 mg, about 25 mg to about 250 mg, about 25 mg to about 225 mg, about 25 mg to about 200 mg, about 25 mg to about 175 mg, or about 25 mg to about 150 mg. In some embodiments, the daily dose may be from about 50 mg to about 450 mg, about 75 mg to about 450 mg, about 100 mg to about 450 mg, about 150 mg to about 450 mg, about 175 mg to about 450 mg, about 200 mg to about 450 mg, about 225 mg to about 450 mg, about 250 mg to about 450 mg, or about 275 mg to about 450 mg.

In embodiments described herein, the daily dose as described above may be administered once per day. In embodiments described herein, the daily dose as described above may be administered in equal amounts twice per day. In embodiments described herein, the daily dose as described above may be administered in equal amounts three times per day. In embodiments described herein, the daily dose as described above may be administered in equal amounts four times per day.

In embodiments described herein, a therapeutically effective amount of a thiolated activated fatty acid may vary as treatment progresses. For example, the daily dose (or dosing regimen) may be increased or decreased as treatment proceeds through administration cycles, or the daily dosage may increase or decrease throughout administration.

The thiolated activated fatty acids described above may be prepared as a pharmaceutically acceptable formulation. The term "pharmaceutically acceptable" is used herein to mean that the compound is appropriate for use in a pharmaceutical product. For example, pharmaceutically acceptable cations include metallic ions and organic ions. More preferred metallic ions include, but are not limited to, appropriate alkali metal salts, alkaline earth metal salts and other physiological acceptable metal ions. Exemplary ions include aluminum, calcium, lithium, magnesium, potassium, sodium and zinc in their usual valences. Preferred organic ions include protonated tertiary amines and quaternary ammonium cations, including in part, trimethylamine, diethylamine, N,N'-dibenzylethylenediamine, chloroprocaine, choline, diethanolamine, ethylenediamine, meglumine (N-methylglucamine) and procaine. Exemplary pharmaceutically acceptable acids include, without limitation, hydrochloric acid, hydroiodic acid, hydrobromic acid, phosphoric acid, sulfuric acid, methanesulfonic acid, acetic acid, formic acid, tartaric acid, maleic acid, malic acid, citric acid, isocitric acid, succinic acid, lactic acid, gluconic acid, glucuronic acid, pyruvic acid, oxalacetic acid, fumaric acid, propionic acid, aspartic acid, glutamic acid, benzoic acid, and the like.

Isomeric and tautomeric forms of thiolated activated fatty acids of the invention as well as pharmaceutically acceptable salts of these compounds are also encompassed by the invention. Exemplary pharmaceutically acceptable salts are prepared from formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, stearic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, cyclohexylaminosulfonic, algenic, β-hydroxybutyric, galactaric and galacturonic acids.

Suitable pharmaceutically acceptable base addition salts used in connection with the thiolated activated fatty acids of the invention include metallic ion salts and organic ion salts. Exemplary metallic ion salts include, but are not limited to, appropriate alkali metal (group Ia) salts, alkaline earth metal (group IIa) salts and other physiological acceptable metal ions. Such salts can be made from the ions of aluminum, calcium, lithium, magnesium, potassium, sodium and zinc. Preferred organic salts can be made from tertiary amines and quaternary ammonium salts, including in part, trimethylamine, diethylamine, N,N'-dibenzylethylenediamine, chloroprocaine, choline, diethanolamine, ethylenediamine, meglumine (N-methylglucamine) and procaine. All of the above salts can be prepared by those skilled in the art by conventional means from the corresponding compound of the present invention.

In embodiments described herein, administering a therapeutically effective amount of a thiolated activated fatty acid, or a pharmaceutically acceptable salt thereof also includes administering a secondary agent. In embodiments described herein, the secondary agent may be selected from a group consisting of an ACE inhibitor, an angiotensin II receptor blocker, or a combination thereof. In some embodiments, the secondary agent may be elanapril. In embodiments described herein, the ACE inhibitor may be selected from a group consisting of perindopril, captopril, enalapril, lisinopril, ramipril, zofenopril, quinapril, benazepril, imidapril, trandolapril, cilazapril, and fosinopril. In embodiments described herein, the angiotensin II receptor blocker may be selected from a group consisting of azilsartan, candesartan, eprosartan, irbesartan, losartan, olmesartan, telmisartan, valsartan, fimasartan, and spironolactone.

In embodiments described herein, the therapeutically effective amount of a secondary agent is from about 2.5 milligrams to less than about 250 milligrams. In embodiments described herein, the daily dose of the secondary agent may be from about 5 mg to about 200 mg, about 10 mg to about 150 mg, about 15 mg to about 100 mg, about 20 mg to about 75 mg, about 25 mg to about 50 mg, or about 30 mg to about 40 mg.

The thiolated activated fatty acids of the invention can be administered in any conventional manner by any route where they are active. Administration can be systemic or local. For example, administration can be, but is not limited to, parenteral, subcutaneous, intravenous, intramuscular, intraperitoneal, transdermal, oral, buccal, or ocular routes, or intranasally, intravaginally, by inhalation, by depot injections, or by implants. In embodiments described herein, the administration may be parenteral or intravenous, all in the presence or absence of stabilizing additives that favor extended systemic uptake, tissue half-life and intracellular delivery. Thus, modes of administration for the compounds of the present invention (either alone or in combination with other pharmaceuticals) can be injectable (including short-acting, depot, implant and pellet forms injected subcutaneously or intramuscularly). In embodiments described herein, an injectable formulation including a thiolated activated fatty acid may be deposited to a site of injury or inflammation, such as, for example, the site of a surgical incision or a site of inflammation due to arthroscopy, angioplasty, stent placement, by-pass surgery and so on.

Various embodiments of the invention are also directed to a method for administering thiolated activated fatty acids. Specific modes of administration may vary and may depend on the indication. The selection of the specific route of administration and the dose regimen may be adjusted or titrated by the clinician according to methods known to the clinician in order to obtain the optimal clinical response. The amount of compound to be administered is that amount which is therapeutically effective. The dosage to be administered will depend on the characteristics of the subject being treated, e.g., the particular animal treated, age, weight, health, types of concurrent treatment, if any, and frequency of treatments, and can be easily determined by one of skill in the art (e.g., by the clinician). Those skilled in the art will appreciate that dosages may be determined with guidance, for example, from Goodman & Gilman's The Pharmacological Basis of Therapeutics, Ninth Edition (1996), Appendix II, pp. 1707-1711 or from Goodman & Gilman's The Pharmacological Basis of Therapeutics, Tenth Edition (2001), Appendix II, pp. 475-493 both of which are hereby incorporated by reference in their entireties. Furthermore, in determining the human equivalent dose from animal studies the U.S. Department of Health and Human Services Food and Drug Administration Center for Drug Evaluation and Research's publication can be used. http://www.fda.gov/downloads/drugs/guidancecomplianceregulatoryinformation/guidances/ucm07 8932.pdf.

Pharmaceutical formulations containing the compounds of the above invention and a suitable carrier can be in various forms including, but not limited to, solids, solutions, powders, fluid emulsions, fluid suspensions, semi-solids, and dry powders including an effective amount of a thiolated activated fatty acid of the invention. It is also known in the art that the active ingredients can be contained in such formulations with pharmaceutically acceptable diluents, fillers, disintegrants, binders, lubricants, surfactants, hydrophobic vehicles, water soluble vehicles, emulsifiers, buffers, humectants, moisturizers, solubilizers, antioxidants, preservatives and the like. The means and methods for administration are known in the art and an artisan can refer to various pharmacologic references for guidance. For example, *Modern Pharmaceutics*, Banker & Rhodes, Marcel Dekker, Inc. (1979); and *Goodman & Oilman's, The Pharmaceutical Basis of Therapeutics,* 6th Edition, MacMillan Publishing Co., New York (1980) both of which are hereby incorporated by reference in their entireties can be consulted.

The compounds of the present invention can be formulated for parenteral or intravenous administration by injection, e.g., by bolus injection or continuous infusion. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents.

Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids diluents such as oleic acid find use in the preparation of injectables. Additional fatty acids diluents that may be useful in embodiments of the invention include, for example, one or more of stearic acid, metallic stearate, sodium stearyl fumarate, fatty acid, fatty alcohol, fatty acid ester, glyceryl behenate, mineral oil, vegetable oil, paraffin, leucine, silica, silicic acid, talc, propylene glycol fatty acid ester, polyethoxylated castor oil, polyethylene glycol, polypropylene glycol, polyalkylene glycol, polyoxyethyleneglycerol fatty ester, polyoxyethylene fatty alcohol ether, polyethoxylated sterol, polyethoxylated castor oil, polyethoxylated vegetable oil, and the like. In some embodiments, the fatty acid diluent may be a mixture of fatty acids. In some embodiments, the fatty acid may be a fatty acid ester, a sugar ester of fatty acid, a glyceride of fatty acid, or an ethoxylated fatty acid ester, and in other embodiments, the fatty acid diluent may be a fatty alcohol such as, for example, stearyl alcohol, lauryl alcohol, palmityl alcohol, palmitolyl acid, cetyl alcohol, capryl alcohol, caprylyl alcohol, oleyl alcohol, linolenyl alcohol, arachidonic alcohol, behenyl alcohol, isobehenyl alcohol, selachyl alcohol, chimyl alcohol, and linoleyl alcohol and the like and mixtures thereof.

Other embodiments of the invention include thiolated activated fatty acid prepared as described above which are formulated as a solid dosage form for oral administration including capsules, tablets, pills, powders, and granules. In such embodiments, the active compound may be admixed with one or more inert diluent such as sucrose, lactose, or starch. Such dosage forms may also comprise, as in normal practice, additional substances other than inert diluents, e.g., lubricating agents such as magnesium stearate. In the case of capsules, tablets, and pills, the dosage forms may also comprise buffering agents and can additionally be prepared with enteric coatings.

In embodiments described herein, the therapeutically effective amount of the thiolated activated fatty acid is in a pharmaceutical composition. Preparation of a thiolated activated fatty acid in solid dosage form may vary. For example, in one embodiment, a liquid or gelatin formulation of the thiolated activated fatty acid may be prepared by combining the thiolated activated fatty acid with one or more fatty acid diluent, such as those described above, and adding a thickening agent to the liquid mixture to form a gelatin. The gelatin may then be encapsulated in unit dosage form to form a capsule. In another exemplary embodiment, an oily preparation of a thiolated activated fatty acid prepared as described above may be lyophilized to form a solid that may be mixed with one or more pharmaceutically acceptable excipient, carrier or diluent to form a tablet, and in yet another embodiment, the thiolated activated fatty acid of an oily preparation may be crystallized to from a solid which may be combined with a pharmaceutically acceptable excipient, carrier or diluent to form a tablet.

Further embodiments which may be useful for oral administration of thiolated activated fatty acids include liquid dosage forms. In such embodiments, a liquid dosage may include a pharmaceutically acceptable emulsion, solution, suspension, syrup, and elixir containing inert diluents commonly used in the art, such as water. Such compositions may also comprise adjuvants, such as wetting agents, emulsifying and suspending agents, and sweetening, flavoring, and perfuming agents.

In still further embodiments, thiolated activated fatty acids of the invention can be formulated as a depot preparation. Such long acting formulations can be administered by implantation (for example, subcutaneously or intramuscularly) or by intramuscular injection. Depot injections can be administered at about 1 to about 6 months or longer intervals. Thus, for example, the compounds can be formulated with suitable polymeric or hydrophobic materials (for example, as an emulsion in an acceptable oil) or ion exchange resins, or as sparingly soluble derivatives, for example, as a sparingly soluble salt.

Other suitable diluents for injectable formulations include, but are not limited to those described below:

Vegetable oil: As used herein, the term "vegetable oil" refers to a compound, or mixture of compounds, formed from ethoxylation of vegetable oil, wherein at least one chain of polyethylene glycol is covalently bound to the vegetable oil. In some embodiments, the amount of ethoxylation can vary from about 2 to about 200, about 5 to 100, about 10 to about 80, about 20 to about 60, or about 12 to about 18 of ethylene glycol repeat units. The vegetable oil may be hydrogenated or unhydrogenated. Suitable vegetable oils include, but are not limited to castor oil, hydrogenated castor oil, sesame oil, corn oil, peanut oil, olive oil, sunflower oil, safflower oil, soybean oil, benzyl benzoate, sesame oil, cottonseed oil, and palm oil. Other suitable vegetable oils include commercially available synthetic oils such as, but not limited to, Miglyol™ 810 and 812 (available from Dynamit Nobel Chemicals, Sweden) Neobee™ M5 (available from Drew Chemical Corp.), Alofine™ (available from Jarchem Industries), the Lubritab™ series (available from JRS Pharma), the Sterotex™ (available from Abitec Corp.), Softisan™ 154 (available from Sasol), Croduret™ (available from Croda), Fancol™ (available from the Fanning Corp.), Cutina™ HR (available from Cognis), Simulsol™ (available from CJ Petrow), EmCon™ CO (available from Amisol Co.), Lipvol™ CO, SES, and HS-K (available from Lipo), and Sterotex™ HM (available from Abitec Corp.). Other suitable vegetable oils, including sesame, castor, corn, and cottonseed oils, include those listed in R. C. Rowe and P. J. Shesky, Handbook of Pharmaceutical Excipients, (2006), 5th ed., which is incorporated herein by reference in its entirety. Suitable polyethoxylated vegetable oils, include but are not limited to, Cremaphor™ EL or RH series (available from BASF), Emulphor™ EL-719 (available from Stepan products), and Emulphor™ EL-620P (available from GAF).

Mineral oils: As used herein, the term "mineral oil" refers to both unrefined and refined (light) mineral oil. Suitable mineral oils include, but are not limited to, the Avatech™ grades (available from Avatar Corp.), Drakeol™ grades (available from Penreco), Sirius™ grades (available from Shell), and the Citation™ grades (available from Avater Corp.).

Castor oils: As used herein, the term "castor oil" refers to a compound formed from the ethoxylation of castor oil, wherein at least one chain of polyethylene glycol is covalently bound to the castor oil. The castor oil may be hydrogenated or unhydrogenated. Synonyms for polyethoxylated castor oil include, but are not limited to polyoxyl castor oil, hydrogenated polyoxyl castor oil, mcrogolglyceroli ricinoleas, macrogolglyceroli hydroxystearas, polyoxyl 35 castor oil, and polyoxyl 40 hydrogenated castor oil. Suitable polyethoxylated castor oils include, but are not limited to, the Nikkol™ HCO series (available from Nikko Chemicals Co. Ltd.), such as Nikkol HCO-30, HC-40, HC-50, and HC-60 (polyethylene glycol-30 hydrogenated castor oil, polyethylene glycol-40 hydrogenated castor oil, polyethylene glycol-50 hydrogenated castor oil, and polyethylene glycol-60 hydrogenated castor oil, Emulphor™ EL-7 19 (castor oil 40 mole-ethoxylate, available from Stepan Products), the Cremophore™ series (available from BASF), which includes Cremophore RH40, RH60, and EL35 (polyethylene glycol-40 hydrogenated castor oil, polyethylene glycol-60 hydrogenated castor oil, and polyethylene glycol-35 hydrogenated castor oil, respectively), and the Emulgin® RO and HRE series (available from Cognis PharmaLine). Other suitable polyoxyethylene castor oil derivatives include those listed in R. C. Rowe and P. J. Shesky, Handbook of Pharmaceutical Excipients, (2006), 5th ed., which is incorporated herein by reference in its entirety.

Sterol: As used herein, the term "sterol" refers to a compound, or mixture of compounds, derived from the ethoxylation of sterol molecule. Suitable polyethoyxlated sterols include, but are not limited to, PEG-24 cholesterol ether, Solulan™ C-24 (available from Amerchol); PEG-30 cholestanol, Nikkol™ DHC (available from Nikko); Phytosterol, GENEROL™ series (available from Henkel); PEG-25 phyto sterol, Nikkol™ BPSH-25 (available from Nikko); PEG-5 soya sterol, Nikkol™ BPS-5 (available from Nikko); PEG-10 soya sterol, Nikkol™ BPS-10 (available from Nikko); PEG-20 soya sterol, Nikkol™ BPS-20 (available from Nikko); and PEG-30 soya sterol, Nikkol™ BPS-30 (available from Nikko). As used herein, the term "PEG" refers to polyethylene glycol.

Polyethylene glycol: As used herein, the term "polyethylene glycol" or "PEG" refers to a polymer containing ethylene glycol monomer units of formula —O—CH2-CH2-. Suitable polyethylene glycols may have a free hydroxyl group at each end of the polymer molecule, or may have one or more hydroxyl groups etherified with a lower alkyl, e.g., a methyl group. Also suitable are derivatives of polyethylene glycols having esterifiable carboxy groups. Polyethylene glycols useful in the present invention can be polymers of any chain length or molecular weight, and can include branching. In some embodiments, the average molecular weight of the polyethylene glycol is from about 200 to about 9000. In some embodiments, the average molecular weight of the polyethylene glycol is from about 200 to about 5000. In some embodiments, the average molecular weight of the polyethylene glycol is from about 200 to about 900. In some embodiments, the average molecular weight of the polyethylene glycol is about 400. Suitable polyethylene glycols include, but are not limited to polyethylene glycol-200, polyethylene glycol-300, polyethylene glycol-400, polyethylene glycol-600, and polyethylene glycol-900. The number following the dash in the name refers to the average molecular weight of the polymer. In some embodiments, the polyethylene glycol is polyethylene glycol-400. Suitable polyethylene glycols include, but are not limited to the Carbowax™ and Carbowax™ Sentry series (available from Dow), the Lipoxol™ series (available from Brenntag), the Lutrol™ series (available from BASF), and the Pluriol™ series (available from BASF).

Propylene glycol fatty acid ester: As used herein, the term "propylene glycol fatty acid ester" refers to an monoether or diester, or mixtures thereof, formed between propylene glycol or polypropylene glycol and a fatty acid. Fatty acids that are useful for deriving propylene glycol fatty alcohol ethers include, but are not limited to, those defined herein. In some embodiments, the monoester or diester is derived from propylene glycol. In some embodiments, the monoester or diester has about 1 to about 200 oxypropylene units. In some embodiments, the polypropylene glycol portion of the molecule has about 2 to about 100 oxypropylene units. In some embodiments, the monoester or diester has about 4 to about 50 oxypropylene units. In some embodiments, the monoester or diester has about 4 to about 30 oxypropylene units. Suitable propylene glycol fatty acid esters include, but are not limited to, propylene glycol laurates: Lauroglycol™ FCC and 90 (available from Gattefosse); propylene glycol caprylates: Capryol™ PGMC and 90 (available from Gatefosse); and propylene glycol dicaprylocaprates: Labrafac™ PG (available from Gatefosse).

Stearoyl macrogol glyceride: Stearoyl macrogol glyceride refers to a polyglycolized glyceride synthesized predominately from stearic acid or from compounds derived predominately from stearic acid, although other fatty acids or compounds derived from other fatty acids may be used in the synthesis as well. Suitable stearoyl macrogol glycerides include, but are not limited to, Gelucire® 50/13 (available from Gattefosse).

In some embodiments, the diluent component comprises one or more of mannitol, lactose, sucrose, maltodextrin, sorbitol, xylitol, powdered cellulose, microcrystalline cellulose, carboxymethylcellulose, carboxyethylcellulose, methylcellulose, ethylcellulose, hydroxyethylcellulose, methylhydroxyethylcellulose, starch, sodium starch glycolate, pregelatinized starch, a calcium phosphate, a metal carbonate, a metal oxide, or a metal aluminosilicate.

Exemplary excipients or carriers for use in solid and/or liquid dosage forms include, but are not limited to:

Sorbitol: Suitable sorbitols include, but are not limited to, PharmSorbidex E420 (available from Cargill), Liponic 70-NC and 76-NC (available from Lipo Chemical), Neosorb (available from Roquette), Partech SI (available from Merck), and Sorbogem (available from SPI Polyols).

Starch, sodium starch glycolate, and pregelatinized starch include, but are not limited to, those described in R. C. Rowe and P. J. Shesky, Handbook of Pharmaceutical Excipients, (2006), 5th ed., which is incorporated herein by reference in its entirety.

Disintegrant: The disintegrant may include one or more of croscarmellose sodium, carmellose calcium, crospovidone, alginic acid, sodium alginate, potassium alginate, calcium alginate, an ion exchange resin, an effervescent system based on food acids and an alkaline carbonate component, clay, talc, starch, pregelatinized starch, sodium starch glycolate, cellulose floc, carboxymethylcellulose, hydroxypropylcellulose, calcium silicate, a metal carbonate, sodium bicarbonate, calcium citrate, or calcium phosphate.

In certain embodiments, the condition to be treated may be, but may not be limited to, inflammatory conditions, obesity, metabolic syndrome, acute kidney disease, chronic kidney disease, atherogenesis, adipogenesis, neointimal proliferation, kidney I/R and xenobiotic injury, focal myocardial I/R injury, Ang II-induced systemic hypertension, pulmonary hypertension, cardiac and pulmonary fibrosis, inflammatory bowel disease, nociception, stroke, motor neuron degeneration, diabetes, asthma, and COPD.

In certain embodiments, the inflammatory condition may be organ preservation for transplantation, osteoarthritis, chronic obstructive pulmonary disease (COPD), atherosclerosis, hypertension, allograft rejection, pelvic inflammatory disease, ulcerative colitis, Crohn's disease, allergic inflammation in the lung, cachexia, stroke, congestive heart failure, pulmonary fibrosis, hepatitis, glioblastoma, Guillain-Barre Syndrome, systemic lupus erythematosus viral myocarditis, posttransplantation organ protection, acute pancreatitis, irritable bowel disease general inflammation, autoimmune disease, autoinflammatory disease, arterial stenosis, organ transplant rejection and burns, chronic lung injury and respiratory distress, insulin-dependent diabetes, non-insulin dependent diabetes, hypertension, obesity, arthritis, neurodegenerative disorders, lupus, Lyme's disease, gout, sepsis, hyperthermia, ulcers, enterocolitis, osteoporosis, viral or bacterial infections, cytomegalovirus, periodontal disease, glomerulonephritis, sarcoidosis, lung disease, lung inflammation, fibrosis of the lung, asthma, acquired respiratory distress syndrome, tobacco induced lung disease, granuloma formation, fibrosis of the liver, graft vs. host disease, postsurgical inflammation, coronary and peripheral vessel restenosis following angioplasty, stent placement or bypass graft, coronary artery bypass graft (CABG), acute and chronic leukemia, B lymphocyte leukemia, neoplastic diseases, arteriosclerosis, atherosclerosis, myocardial inflammation, psoriasis, immunodeficiency, disseminated intravascular coagulation, systemic sclerosis, amyotrophic lateral sclerosis, multiple sclerosis, Parkinson's disease, Alzheimer's disease, encephalomyelitis, edema, inflammatory bowel disease, hyper IgE syndrome, cancer metastasis or growth, adoptive immune therapy, reperfusion syndrome, radiation burns, alopecia areta, ischemia, myocardial infarction, arterial stenosis, rheumatoid arthritis, coronary restenosis, neurocognitive decline and insulin resistance.

In embodiments described herein, the method of treating inflammation, obesity, metabolic syndrome, acute kidney disease, and chronic kidney disease comprises administering to a subject in need thereof an effective amount of a thiolated activated fatty acid and a pharmaceutically acceptable excipient.

In embodiments described herein, the method of treating inflammation, obesity, metabolic syndrome, acute kidney disease, and chronic kidney disease comprises administering to a subject in need thereof an effective amount of a thiolated activated fatty acid and a pharmaceutically acceptable excipient, wherein the thiolated activated fatty acid provides an exended release of a activated fatty acid.

In embodiments described herein, the method of treating inflammation, obesity, metabolic syndrome, acute kidney disease, and chronic kidney disease comprises administering to a subject in need thereof an effective amount of a thiolated activated fatty acid and a pharmaceutically acceptable excipient, wherein the reduction of a activated fatty acid alkene by prostaglandin reductase 1 is prevented.

In embodiments described herein, the method of treating inflammation, obesity, metabolic syndrome, acute kidney disease, and chronic kidney disease comprises administering to a subject in need thereof an effective amount of a thiolated activated fatty acid and a pharmaceutically acceptable excipient, wherein the adduction of a activated fatty acid with glutathione is delayed.

In embodiments described herein, the method of treating inflammation comprises administering to a subject in need thereof an effective amount of a thiolated activated fatty acid and a pharmaceutically acceptable excipient, wherein the negative side effects of a subject's gastrointestinal tract are reduced. The side effects of the gastrointestinal tract may include diarrhea, cramping irritation, inflammatory bowel disease, colitis, and ulcers.

The present invention, thus generally described, will be understood more readily by reference to the following examples, which are provided by way of illustration and are not intended to be limiting of the present invention.

EXAMPLES

Example 1

An exemplary thiolated electrophilic fatty acid was synthesized by direct reaction of nitro-oleic acid with 3-5 fold excess sodium sulfide or sodium hydrosulfide in a solution of methanol and pH 9 phosphate buffer. Nitro-oleic ($NO_2$—OA) acid was dissolved in methanol for solubility and added slowly to a solution of sulfide in buffer, then stirred at room temperature for two hours under a nitrogen atmosphere. The reaction was quenched and stirred briefly with dilute acid and saturated aqueous ammonium chloride, then partitioned and extracted with diethyl ether. The solution was worked up by standard methods and purified by flash chromatography. The products were identified as dimers, a combination of diastereomers with a variable number of bridging sulfur atoms through NMR and LCMS analysis.

The purified thiolated $NO_2$—OA was then tested whether it would express the desired gene expression modulation and antioxidant phenotype in murine macrophage cells (RAW264.7). This was reflected by the increased activation of the Nrf2-dependent transcription of heme oxygenase 1, NAD(P)H dehydrogenase quinone 1 and glutamate-cysteine ligase modifier subunit compared to controls. Thiolated $NO_2$—OA induced a dose-dependent antioxidant response in RAW264.7 cells similar to that of $NO_2$—OA at 4 and 8 hours. However, at later time points the induction of genes activated by thiolated $NO_2$—OA was much greater than $NO_2$—OA treatment (16 and 24 hours). Additionally, high performance liquid chromatography-tandem mass spectrometry analysis showed that thiolated $NO_2$—OA liberates free $NO_2$—OA that then displays a similar beta-oxidation and fatty acid saturation profile. These results support that thiolated $NO_2$—OA can be a viable prodrug candidate that avoids first pass drug inactivation by the gastrointestinal tract and liver, and upon reversal of the thiolation product displays a metabolic and biological profile similar to free $NO_2$—OA.

Summary: OA-$NO_2$—$S_x$ prodrug successfully synthesized and purified, NMR spectra shown in FIG. 1, Nrf2-dependent genes (HO-1, NQO-1, GCLM) are induced by OA-$NO_2$—$S_x$ and the metabolic profile of OA-$NO_2$—$S_x$ indicates release and metabolism of OA-NO2 from the prodrug.

Figure 2:
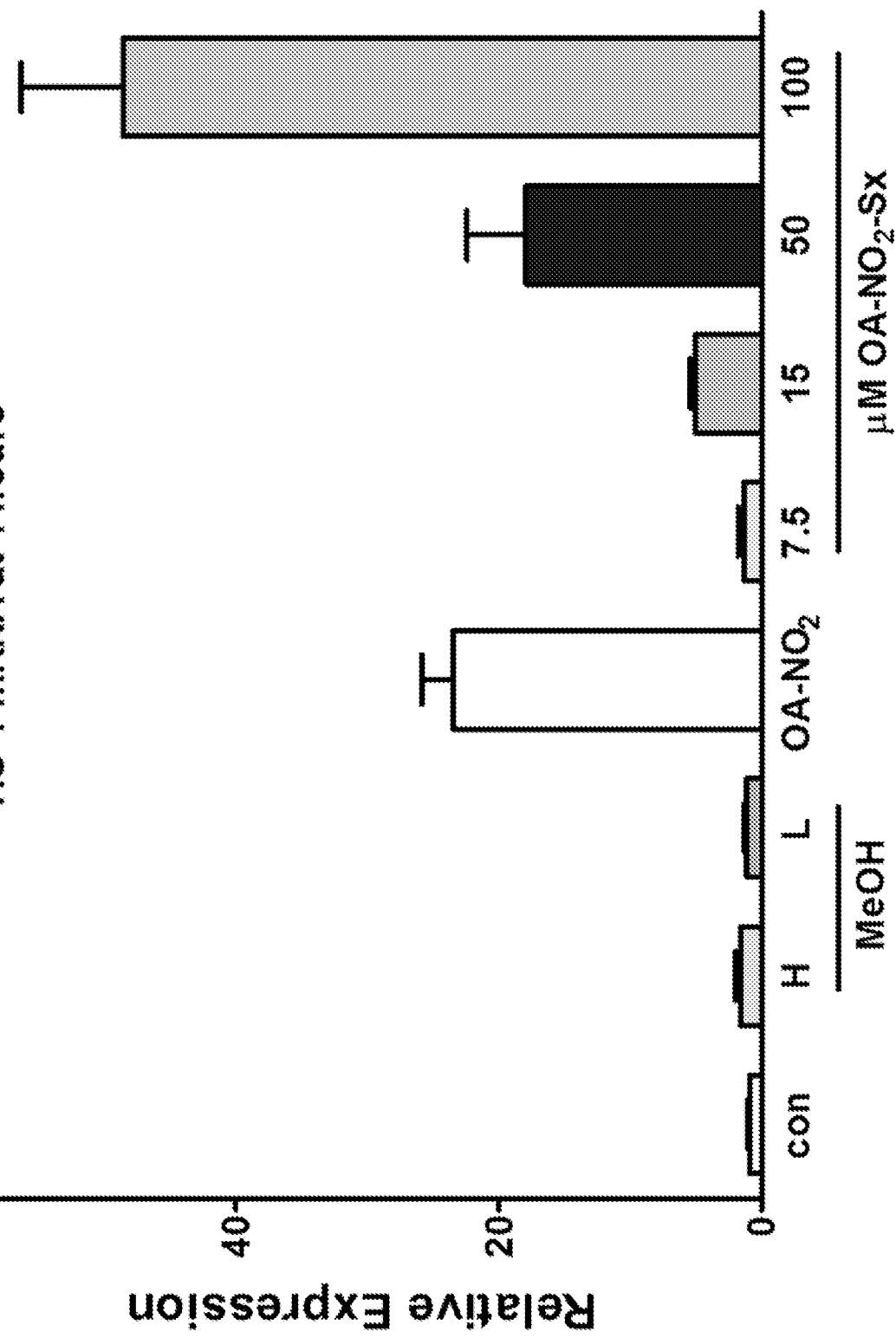
FIG. 2: HO-1 Transcription Induced by $OA-NO_2-S_x$.
Figure 3:
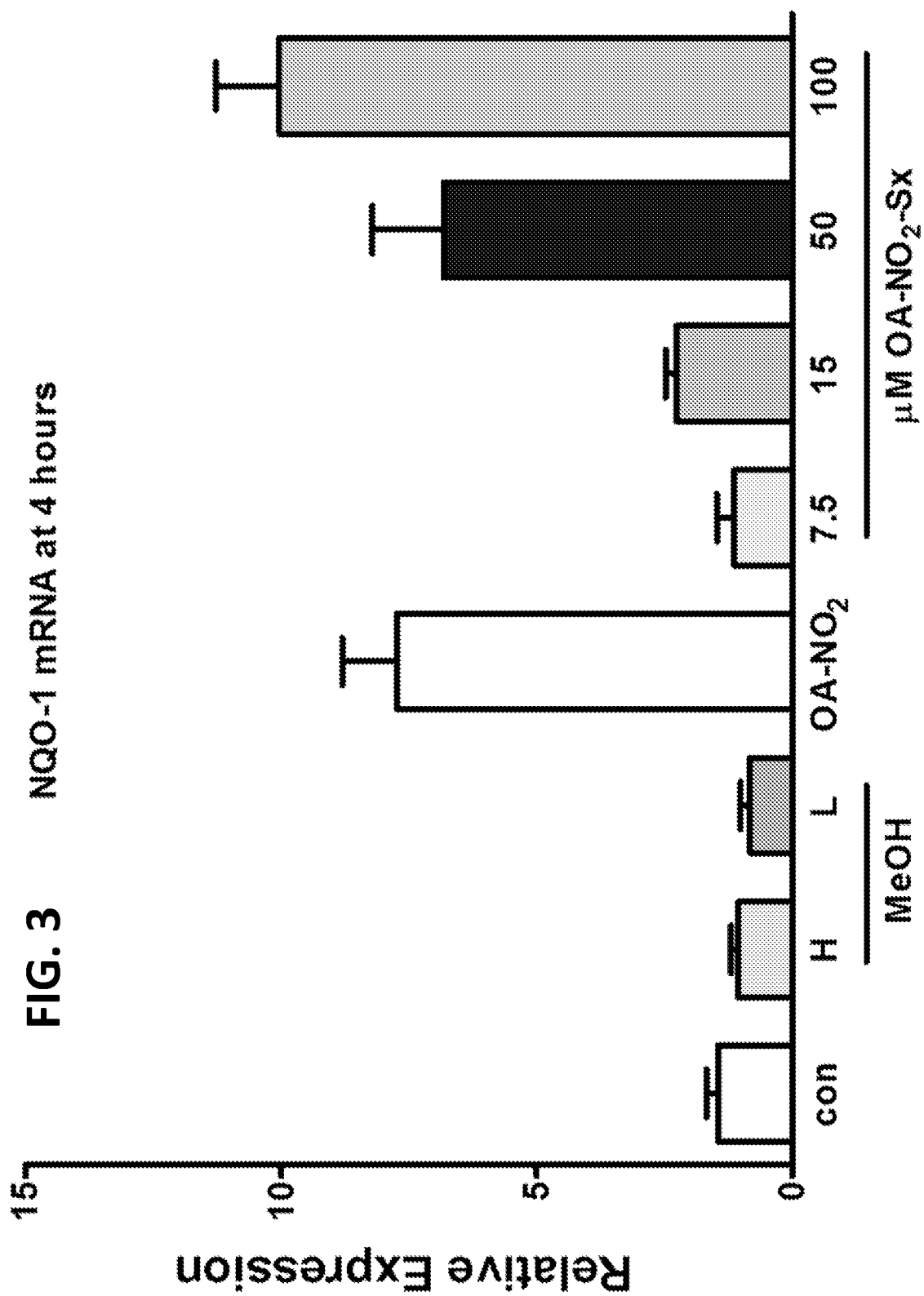
FIG. 3: NQO-1 Transcription Induced by $OA-NO_2-S_x$.
Figure 4:
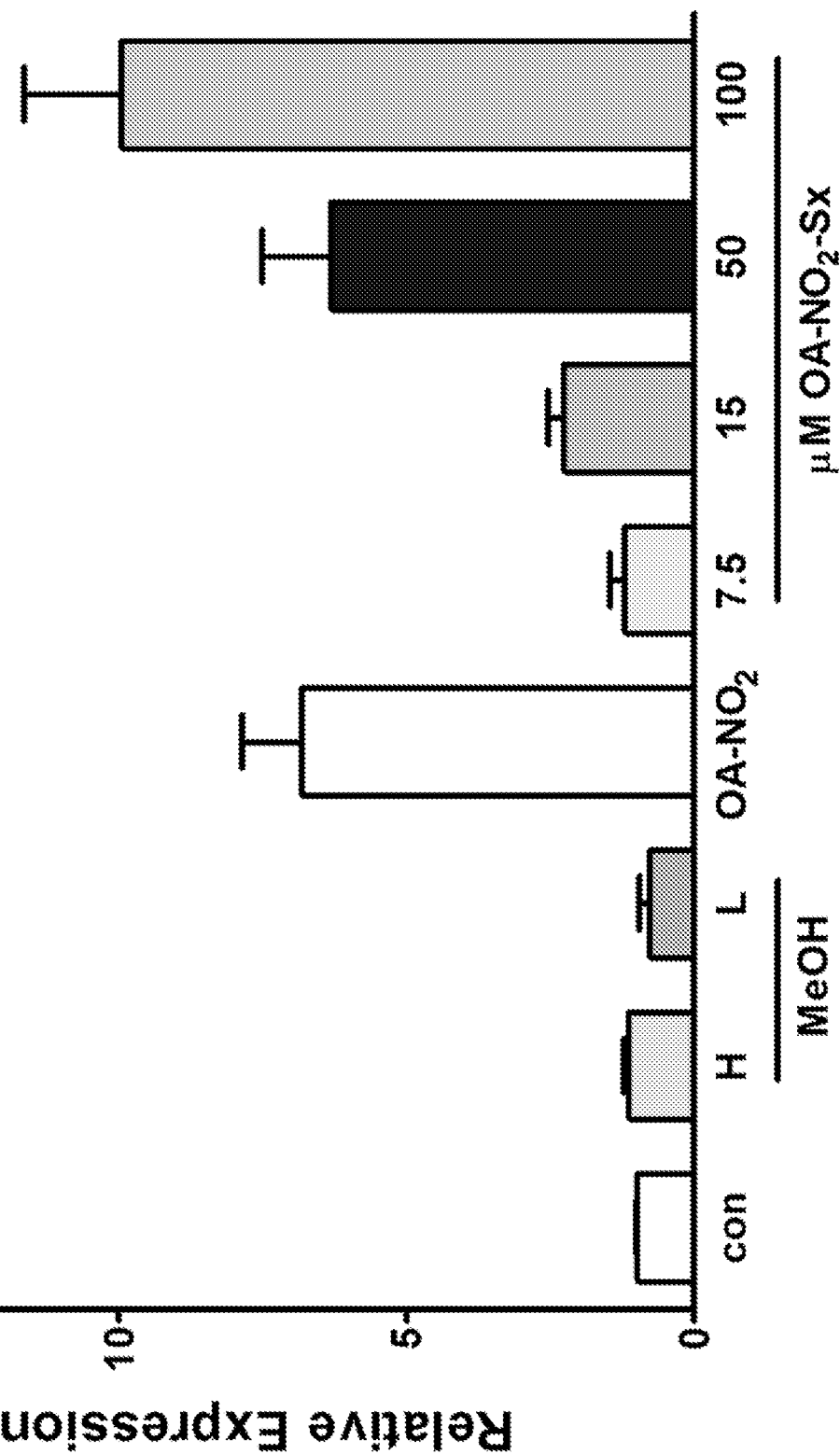
FIG. 4: GCLM Transcription Induced by $OA-NO_2-S_x$.

Murine macrophage cells (RAW264.7) were treated with the purified thiolated $NO_2$—OA for 4 hours. RNA was extracted using the Trizol method, quantified using nanodrop technology, reversed transcribed into cDNA and then quantitative PCR was performed using Taqman assays. There was a dose-dependent increase of Nrf2-dependent transcription of heme oxygenase 1 (HO-1, FIG. 2), NAD (P)H dehydrogenase quinone 1 (NQO-1, FIG. 3) and glutamate-cysteine ligase modifier subunit (GCLM, FIG. 4) following treatment of thiolated $NO_2$—OA for 4 hours compared to controls (media change or low or high concentrations of methanol, which was used as vehicle to solvate the OA-$NO_2$ or OA-$NO_2$—Sx). The concentration of 50 µM OA-$NO_2$—Sx induced a similar Nrf2 activation profile for HO-1, NQO-1 and GCLM (18.0-, 6.8- and 6.3-fold, respectively) as 5 µM OA-$NO_2$ (23.5-, 7.7-, 6.8-fold for HO-1, NQO1 and GCLM, respectively) at the 4 hour time point.

Experimental details: In every experiment, RAW264.7 cells were treated with 7.5, 15, 50 and 100 µM OA-$NO_2$—$S_x$, 5 µM OA-$NO_2$ two concentrations of methanol (MeOH) to match the lowest and highest amount of vehicle (5 and 100 µM) and a media control only. Within each experiment, there were two or three biological replicates per treatment group. After treatment, RNA was extracted using the Trizol method, quantified using nanodrop technology, reversed transcribed into cDNA and then quantitative PCR (qPCR) was performed using Taqman assays. In each qPCR experiment, there were two technical replicates per sample of RNA. The two technical replicates were then averaged for each biological replicate. The bars in the graph represent mean±standard error of the mean (SEM) of the biological replicates.

Results: Increase in Nrf2-dependent transcription Heme Oxygenase 1 (HO-1), NAD(P)H Quinone Dehydrogenase 1 (NQO-1) and Gamma-glutamyl Cystenyl Ligase (GCLM) following the treatment of OA-$NO_2$—Sx and OA-$NO_2$ in RAW264.7 cells for 4 hours.

Figure 5:
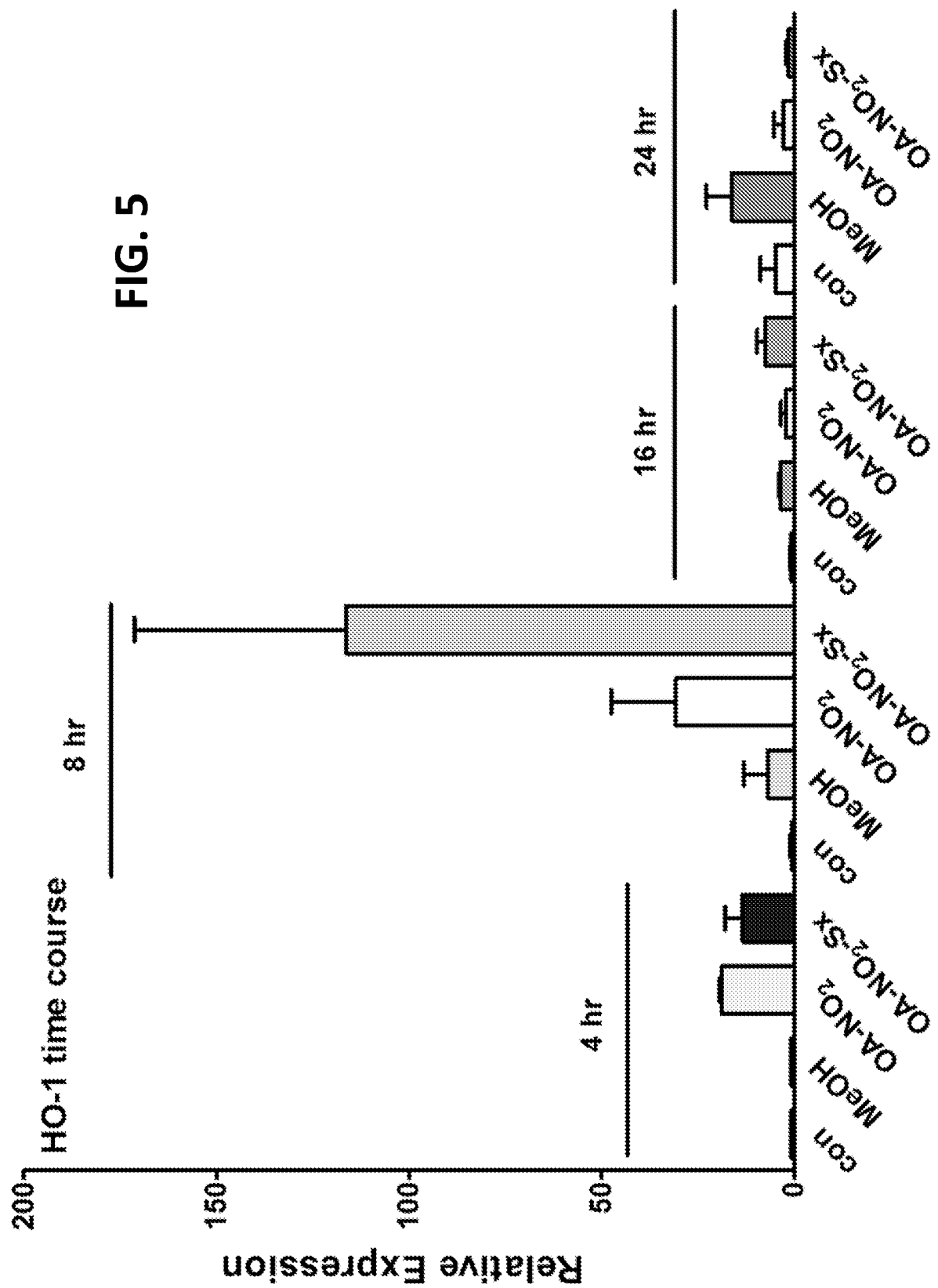
FIG. 5: HO-1 Transcription Induced by $OA-NO_2-S_x$ over time course.

Murine macrophage cells (RAW264.7) were treated with 50 µM OA-$NO_2$—Sx, 5 µM OA-$NO_2$, MeOH (the highest amount of vehicle added to RAW cells to match the highest concentration, which is 50 µM for OA-$NO_2$—Sx) and media alone for 4, 8, 16 and 24 hours. RNA was extracted at each time point using the Trizol method, quantified using nanodrop technology, reversed transcribed into cDNA and then quantitative PCR was performed using Taqman assays. In FIG. 5, HO-1 steady-state mRNA levels reached maximum around 8 hours for both OA-$NO_2$—Sx (116.5-fold) and OA-$NO_2$ (30.7-fold) compared to media and vehicle controls and returned to basal levels by 24 hours. At 16 hours, HO-1 mRNA levels were still significantly elevated with OA-$NO_2$—Sx treatment (7.5-fold) whereas OA-$NO_2$ treatment returned to baseline (similar to media and vehicle controls). In FIG. 6, NQO-1 mRNA levels peaked between 8 and 16 hours for OA-$NO_2$ (115.0- and 98.9-fold, respectively) However NQO-1 mRNA levels were significantly higher with OA-$NO_2$—Sx compared to OA-$NO_2$ at 16 hours (701.1-fold for OA-$NO_2$—Sx vs 98.9-fold for OA-$NO_2$). There was a similar trend for GCLM mRNA levels (FIG. 7) remained elevated for OA-$NO_2$—Sx (30.0-fold) compared to 1.7-fold for 5 µM OA-$NO_2$ treatment at 16 hours. The data in FIGS. 5-7 demonstrate that at later time points the induction of genes activated by thiolated $NO_2$—OA was much greater than $NO_2$—OA treatment (mainly at 8 and 16 hours and to a lesser extent at 24 hours), which suggest thiolated $NO_2$—OA is a viable prodrug.

Experimental details: Murine macrophage cells (RAW264.7) were treated with 50 µM OA-$NO_2$—Sx, 5 µM OA-NO$_2$, MeOH (the highest amount of vehicle added to RAW cells to match the highest concentration, which is 50 µM for OA-NO$_2$—Sx) and media alone for 4, 8, 16 and 24 hours. RNA was extracted at each time point using the Trizol method, quantified using nanodrop technology, reversed transcribed into cDNA and then quantitative PCR for HO-1, NQO-1 and GCLM (multiplexed with actin) was performed using Taqman assays. Within each independent experiment, every treatment had at least two biological replicates at each time point. The data represents two independent experiments as mean±SEM.

Results: Time course of Heme Oxygenase 1 (HO-1), NAD(P)H Quinone Dehydrogenase 1 (NQO-1) and Gamma-glutamyl Cystenyl Ligase (GCLM) following treatment of 50 µM OA-NO$_2$—Sx or 5 µM OA-NO$_2$ for 4, 8, 16 and 24 hours.

What is claimed is:

1. A composition comprising an effective amount of a thiolated nitro fatty acid of the formula:

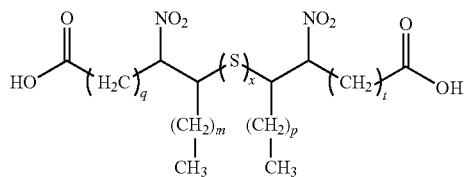

wherein x is 1 to 5; and q, m, p and t are, independently, 1 to 10; and
a pharmaceutically acceptable excipient.

2. A method for treating an inflammatory condition, obesity, metabolic syndrome, acute kidney disease, chronic kidney disease, atherogenesis, adipogenesis, neointimal proliferation, kidney I/R and xenobiotic injury, focal myocardial I/R injury, Ang II-induced systemic hypertension, pulmonary hypertension, cardiac and pulmonary fibrosis, inflammatory bowel disease, nociception, stroke, motor neuron degeneration, diabetes, asthma, or COPD comprising administering to a subject in need thereof a thiolated nitro fatty acid of the formula:

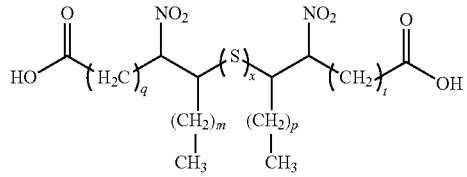

wherein x is 1 to 5; and q, m, p and t are, independently, 1 to 10; and
a pharmaceutically acceptable excipient.

3. The method of claim 2, wherein the thiolated nitro fatty acid provides an extended release of a nitro fatty acid.

4. The method of claim 3, wherein the thioloated nitro fatty acid releases the nitro fatty acid and a hydrogen sulfide, further providing additional protective measures.

5. The method of claim 2, wherein the reduction of a nitro fatty acid alkene is prevented.

6. The method of claim 2, wherein the adduction of a nitro fatty acid with glutathione is delayed.

7. The method of claim 2, wherein side effects from nitro fatty acids are reduced.

8. The method of claim 7, wherein the side effects of the gastrointestinal tract is selected from the group consisting of diarrhea, cramping irritation, inflammatory bowel disease, colitis, and ulcers.

9. The method of claim 2, wherein the subject is treated for an inflammatory condition, obesity, metabolic syndrome, acute kidney disease, or chronic kidney disease.

10. The method of claim 2, wherein the administered thiolated nitro fatty acid releases a nitro fatty acid.

11. The method of claim 2, wherein the administered thioloated nitro fatty acid releases a nitro fatty acid and a hydrogen sulfide.

12. The composition of claim 1, wherein the thiolated nitro fatty acid is:

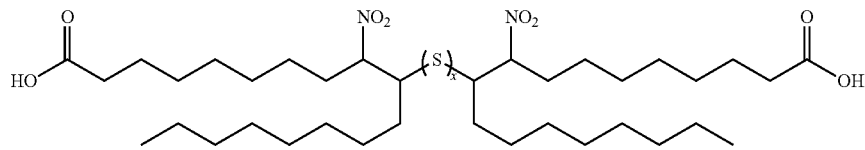

wherein x is 1 to 5.

13. The composition of claim 1, wherein the thiolated nitro fatty acid is:

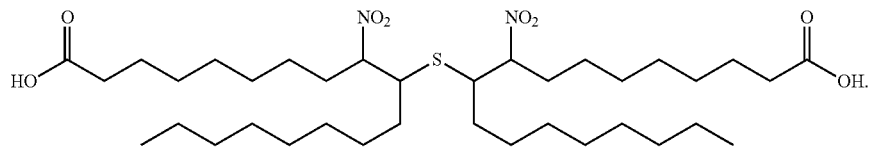

14. The method of claim 2, wherein the thiolated nitro fatty acid is:

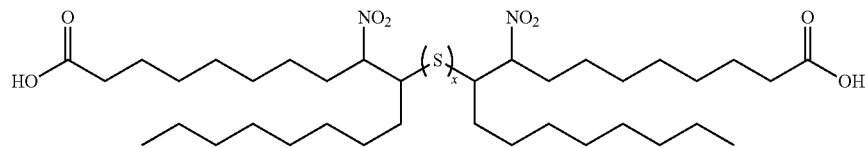

wherein x is 1 to 5.

15. The method of claim 2, wherein the thiolated nitro fatty acid is:

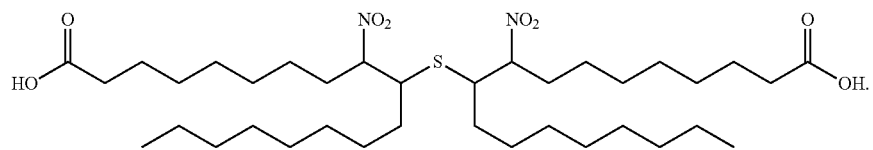 [SMILES: CCCCCCCCC(SC(CCCCCCCC)C(CCCCCCCC(=O)O)[N+](=O)[O-])C(CCCCCCCC(=O)O)[N+](=O)[O-]]

16. The method of claim 14, wherein the subject is treated for an inflammatory condition, obesity, metabolic syndrome, acute kidney disease, or chronic kidney disease.

17. The method of claim 15, wherein the subject is treated for an inflammatory condition, obesity, metabolic syndrome, acute kidney disease, or chronic kidney disease.

\* \* \* \* \*